(12) United States Patent
Scilimati et al.

(10) Patent No.: US 7,989,450 B2
(45) Date of Patent: Aug. 2, 2011

(54) FUNCTIONALIZED DIARYLISOXAZOLES INHIBITORS OF CICLOOXYGENASE

(75) Inventors: Antonio Scilimati, Bari (IT); Paola Vitale, Bari (IT); Leonardo Di Nunno, Bari (IT); Paola Patrignani, Chieti (IT); Stefania Tacconelli, Chieti (IT); Marta Luciana Capone, Chieti (IT)

(73) Assignees: Universita' Degli Studi Di Bari, Bari (IT); Universita' Degli Studi "G.D.'Annunzio"—Chieti, Chieti (IT)

( * ) Notice: Subject to any disclaimer, the term of this patent is extended or adjusted under 35 U.S.C. 154(b) by 268 days.

(21) Appl. No.: 12/007,571

(22) Filed: Jan. 11, 2008

(65) Prior Publication Data

US 2009/0181970 A1  Jul. 16, 2009

(51) Int. Cl.
*A61K 31/42* (2006.01)
*A61K 31/5355* (2006.01)
*C07D 261/08* (2006.01)
*C07D 413/06* (2006.01)

(52) U.S. Cl. .............. 514/236.8; 514/378; 544/137; 548/247

(58) Field of Classification Search .................. 548/247
See application file for complete search history.

(56) References Cited

U.S. PATENT DOCUMENTS

| | | | |
|---|---|---|---|
| 4,327,222 A | 4/1982 | Micetich et al. | |
| 5,318,970 A | 6/1994 | Suzuki et al. | |
| 5,399,577 A | 3/1995 | Shindo et al. | |
| 5,859,257 A | 1/1999 | Talley | |
| 5,985,902 A | 11/1999 | Talley et al. | |
| 2005/0131028 A1* | 6/2005 | Carter et al. | 514/341 |

FOREIGN PATENT DOCUMENTS

| | | |
|---|---|---|
| EP | 0 026 928 A | 4/1981 |
| EP | 0 549 797 A | 7/1993 |
| EP | 0 633 254 A | 1/1995 |
| EP | 1 251 126 A | 10/2002 |
| WO | WO 96/25405 A | 8/1996 |
| WO | WO 98/47880 A | 10/1998 |
| WO | WO 01/81332 A | 11/2001 |
| WO | WO 02/083655 A | 10/2002 |
| WO | WO 03/029230 A | 4/2003 |
| WO | WO 03/031404 A | 4/2003 |
| WO | WO 03/078408 A | 9/2003 |
| WO | WO 03/087062 A | 10/2003 |
| WO | WO 2004/017968 A | 3/2004 |
| WO | WO 2004/037798 A | 5/2004 |
| WO | WO 2005/007620 A | 1/2005 |
| WO | WO 2005/068442 | 7/2005 |

OTHER PUBLICATIONS

Imanishi, et al. Document No. 145:505447, retrieved from CAPLUS on Feb. 26, 2010.*
Cho, et al. Document No. 140:339321, retrieved from CAPLUS on Feb. 26, 2010.*
Reddy, et al. Document No. 138:321278, retrieved from CAPLUS on Feb. 26, 2010.*
Wakefield. Document No. 138:368783, retrieved from CAPLUS on Feb. 26, 2010.*
Navarro-Ocana, et al. Document No. 125:195484 retrieved from CAPLUS on Feb. 26, 2010.*
Toyokuni, et al. Bioorganic and Medicinal Chemistry Letter. (2005), 15, 4699-4702.*
Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.orglwikilCancer.*
Document 145:505447, retrieved from CALPUS on Oct. 7, 2010.*
Document No. 93:149330, retrieved from CALPUS on Oct. 7, 2010.*
Document No. 67:100041, retrieved from CALPUS on Oct. 7, 2010.*
International Search Report in PCT/IB2005/000047 dated Sep. 28, 2005.
Database CA Online; Chemical Abstracts Service, Columbus Ohio; Davies, Mark W. et al, "A regioselective cycloaddition route . . . ", XP002335580; retrieved from STN Database accession No. 2001:603098 Chem. Abs. RN 374715-26-1 Abstract & Chemical Communications, vol. 17, 2001, pp. 1558-1559.
Roston et al, "Comparison of drug substance impurity profiles generated with extended length columns during packed—column SFC", Journal of Pharmaceutical and Biomedical Analysis, vol. 26, No. 3, 2001, pp. 339-355, XP002335573, Figure 1.
Talley et al, "4-'5-Methyl-3-phenylisoxazol-4-yl!-benzenesulfonamide, Valdecoxib: A Potent and Selective Inhibitor of COX-2", Journal of Medicinal Chemistry, vol. 43, No. 5, 2000, pp. 775-777; XP002335574, p. 775.
Talley et al, "N-' '(5-Methy1-3-phenylisoxazol-4-yl)-phenyl!sulfonyl!propanamide, sodium salt, parecoxib sodium: a potent and selective inhibitor of COX-2 for parenteral administration", Journal of Medicinal Chemistry Scheme 1, vol. 43, No. 9, 2000, pp. 1661-1663, XP002335575 Scheme 1.
Database CA Online, Chemical Abstracts Service, Columbus, Ohio, Bellec et al, "Preparation of trisubstituted isoxazoles by chemical and electrochemical reduction . . . ", XP002335581 retrieved from STN Database accession No. 1980:426329 Chem. Abs. RNs 37928-17-9, 74048-23-0 abstract.
Di Nunno et al, "Regioselective synthesis and side-chain metallation and elaboration of . . . ", Tetradedron, Elsevier Science Publishers, Amsterdam, NL, vol. 58, No. 13, Mar. 25, 2002, pp. 2659-2665, XP004344987.
Di Nunno et al, "Novel Synthesis of 3,4-Diarylisoxazole . . . ", Journal of Medicinal Chemistry, vol. 47, No. 20, 2004, pp. 4881-4890, XP002335576.

* cited by examiner

*Primary Examiner* — Shawquia E Young
(74) *Attorney, Agent, or Firm* — Nixon & Vanderhye P.C.

(57) ABSTRACT

Isoxazole derivatives, in particular diarylisoxazole derivatives inhibitors of cyclooxygenase (COX), in particular cyclooxygenase-1 (COX-1), their pharmaceutical compositions, the process for their preparation and their use for the chemoprevention and treatment of inflammatory syndromes and in the prevention and treatment of carcinomas, in particular intestinal, ovarian and cutaneous carcinomas, in the treatment of pain syndromes, in particular after surgery, and in the cardiovascular field as antithrombotics/vasoprotectives/cardioprotectives.

2 Claims, No Drawings

FUNCTIONALIZED DIARYLISOXAZOLES INHIBITORS OF CICLOOXYGENASE

STATE OF THE ART

The term "non-steroidal anti-inflammatory drugs" (NSAID) refers to a class of drugs known for a long time that is able to reduce inflammation, pain and fever. The term "non-steroidal" distinguishes these drugs from corticosteroids with an anti-inflammatory activity, which are agents with a more marked anti-inflammatory action, but which present significant and important side effects. The most known and used drugs belonging to the class of non-steroidal anti-inflammatory drugs (NSAID) are for example acetylsalicylic acid (ASA) (Aspirin®) and the corresponding salicylates, ibuprofen, naproxen and indomethacin. In particular, the properties of acetylsalicylic acid (ASA) as an anti-inflammatory agent have been known for a long time, but in the last decades the efficacy of low doses (75-150 mg/day) of acetylsalicylic acid as an antithrombotic has been demonstrated. Recent experimental evidence bear out the hypothesis that the cardioprotection of low doses of acetylsalicylic acid is the result of an almost complete and persistent suppression of the biosynthesis of platelet thromboxane $(TX)A_2$, due to the irreversible inhibition of the activity of cyclooxygenase-1 (COX-1). This complete and persistent inhibition is necessary as it has been demonstrated that even small concentrations of (TX) $A_2$ are able to provoke platelet activation.

A meta-analysis of more than 50 clinical studies of secondary prevention carried out on various groups of patients, the Antiplatelets Trialist's Collaboration, shows that aspirin can prevent vascular death by about 15-20%, and non fatal vascular events by about 25-30%. Possible causes involved in aspirin's failure to prevent a larger number of events may be the participation of extra-platelet mechanisms in occlusive vascular events and/or the contribution of platelet agonists such as ADP and isoprostanes, mechanisms that are not influenced by treatment with acetylsalicylic acid. Moreover, heterogenicity in the suppression of the activity of platelet COX-1—seen in patients with cardiovascular diseases—could be involved in the small or moderate reduction of risk. Recent data suggest that, in some subjects, a reduced efficacy of acetylsalicylic acid in inhibiting the synthesis of $(TX)A_2$ in vivo, is associated with a higher risk of myocardial infarction or of death in patients with cardiovascular diseases. Many mechanisms may participate in this incomplete inhibition of platelet COX-1 by acetylsalicylic acid.

It is therefore clearly important to make available new cyclooxygenase-inhibiting compounds, which exert a "protective" action on the cardiovascular system similar to that of acetylsalicylic acid and which may be used, for example, in ASA-resistant patients.

Moreover, it has been shown that COX-1 plays a significant role in the development of cancer pathologies, in particular in the development of intestinal polyposes and in the onset of cutaneous and ovarian carcinomas. In parallel, it has also been seen that COX-1 plays an important role in the onset, for example after surgery, of states of pain of medium and strong entity. It is therefore important to select and identify new powerful and selective inhibitors of COX-1.

AIMS OF THE INVENTION

The aim of the present invention is to make available a class of compounds that inhibit cyclooxygenase (COX), in particular diarylisoxazole derivatives, with pharmacological activity in the treatment of inflammatory syndromes and in the treatment of pain syndromes, which are also efficacious in modulating platelet aggregation and therefore possess antithrombotic/vasoprotective/cardioprotective activity.

Another aim of the present invention is to make available a class of compounds that inhibit cyclooxygenase (COX), in particular diarylisoxazole derivatives, which can be used advantageously as chemotherapy agents and in the prevention of diseases affecting the cardiovascular apparatus, both in patients at risk and in healthy people.

Another aim of the present invention is to make available a process for preparing a class of compounds that inhibit cyclooxygenase (COX), in particular diarylisoxazole derivatives, which is simple, which consists of a limited number of steps and can be applied from the industrial point of view.

A further aim of the present invention is to make available a pharmaceutical composition that comprises at least one inhibitor of cyclooxygenase (COX), in particular a diarylisoxazole derivative, which can be effectively used in chemoprevention, in the treatment of inflammatory syndromes, in the prevention and treatment of carcinomas, in particular intestinal, ovarian and cutaneous carcinomas, in the treatment of pain syndromes, in particular after surgery, and which may be further used for the prevention of damage to the cardiovascular apparatus.

The aim of the invention is also to make available a class of compounds that inhibit cyclooxygenase (COX), in particular diarylisoxazole derivatives, that show high half-life, low renal toxicity, high analgesic, anti-inflammatory and chemopreventive activity.

DESCRIPTION OF THE INVENTION

These and other aims and respective advantages that will be better explained by the following description are achieved by compounds that inhibit cyclooxygenase (COX), in particular diarylisoxazole derivatives, having the following general formula (1):

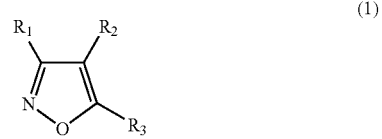

where:
$R_1$=aryl, substituted aryl or heteroaryl, substituted heteroaryl, saturated or unsaturated carbocycle or heterocycle
$R_2$=aryl, substituted aryl or heteroaryl, substituted heteroaryl, $(CH_2)_nG$;
$R_3$=$(CH_2)_nG$, aryl, substituted aryl or heteroaryl, substituted heteroaryl, $CF_3$, $(COO(CH_2)_3(NOC_4H_8)$, $COO(CH_2)_3Br)$;
n=0-5
G=H, $C_1$-$C_5$ alkyl, $YR^I$, Halogen, $COR^{II}$, $ONO_2$, morpholine, other NO-donor groups
Y=O, NH, S;
$R^I$=H, $C_1$-$C_5$ alkyl, $COR^{III}$;
$R^{III}$=H, $C_1$-$C_5$ alkyl
$R^{II}$=$C_1$-$C_5$ alkyl, $YR^{IV}$
$R^{IV}$=H, $C_1$-$C_5$ alkyl, $(CH_2)_nZ$;
Z=Halogen, $ONO_2$, morpholine, other NO-donor groups,
$R_1$, $R_2$ and $R_3$ may be independently equal or different to one another.

Preferably, $R_3$ is a linear, branched, substituted, not substituted $C_1$-$C_5$ alkyl chain; a linear, branched, substituted, not substituted $C_1$-$C_5$ alkenyl chain; a linear, branched, substituted, not substituted $C_1$-$C_5$ alkynyl chain and $R_1$ and $R_2$ are defined as above, $R^I$, $R^{II}$, $R^{III}$ and $R^{IV}$ are independently equal or different to one another and are chosen as a linear, branched, substituted, not substituted $C_1$-$C_5$ alkyl chain; a linear, branched, substituted, not substituted $C_1$-$C_5$ alkenyl chain; a linear, branched, substituted, not substituted alkynyl chain $C_1$-$C_5$ and $R^{II}$ may also be chosen between H, OH.

$R_1$ and $R_2$ are aryl, substituted aryl (where the term "aryl" also includes heterocyclic compounds derived from arenes by substitution of one or more groups (—C=) and/or (—CH=CH—) with trivalent or divalent heteroatoms in order to maintain the electronic system characteristic of aromatic systems), with $R_1$ and $R_2$ independently equal or different to one another.

Or $R_1$ is a saturated or unsaturated, substituted and not substituted carbocycle or heterocycle.

In particular, $R_3$ is chosen among: $CH_3$, $CH_3CH_2$, $CF_3$, COOH, COOCH$_3$, COO(CH$_2$)$_3$(NOC$_4$H$_8$) [by (NOC$_4$H$_8$) we mean the morpholine group], COO(CH$_2$)$_3$Br, COO(CH$_2$)$_3$ONO$_2$, CH$_2$OH, CH$_2$OCOCH$_3$.

Always according to the invention, $R_1$ and $R_2$ are advantageously chosen among: phenyl, 5-bromo-2-furyl, 5-chloro-2-furyl, 5-methyl-2-furyl, chlorophenyl, fluorophenyl and tetrahydrofuranyl.

Diarylisoxazole derivatives, with general formula (1) according to the present invention, may be advantageously prepared by a reaction of cycloaddition of aryl nitrile oxides with ketone or alkyne enolates, for example as described in:

Quilico, A.; Speroni, G. *Gazz. Chim. Ital.* 1946, 76, 148. Quilico, A.; Simonetta, M. *Gazz. Chim. Ital.* 1946, 76, 200. Quilico, A.; Stagno D'Alcontres, G. *Gazz. Chim. Ital.* 1949, 79, 654. Bast, K.; Christl, M.; Huisgen, R.; Mack, W.; Sustmann, R. *Chem. Ber.* 1973, 106, 3258. Christl, M.; Huisgen, R.; Sustmann, R. *Chem. Ber.* 1973, 106, 3275. Huisgen, R.; Christl, M. *Chem. Ber.* 1973, 106, 3291. Huisgen, R. *J. Org. Chem.* 1976, 41, 403. Grundmann, C.; Kite, G. F. *Synthesis* 1973, 156. Caramella, P.; Grunanger, P. In 1,3-*Dipolar Cycloaddition Chemistry*; Padwa, A, Ed.; Wiley Interscience: New York, 1984; Vol. I, p 291.

In general terms, they are advantageously prepared by reaction between aryl nitrile oxides and free enolate ions (in turn obtained by a metallation reaction of various ketones with LDA or NaH in suitable conditions), followed where necessary by a dehydration/aromatisation reaction and possibly by further derivatisation/modification reactions of the derivatives thus obtained, for example as described in:

Di Nunno, L.; Scilimati, A.; Vitale, P. Regioselective synthesis and side-chain metallation and elaboration of 3-aryl-5-alkylisoxazoles. *Tetrahedon* 2002, 58, 2659-2665. Di Nunno, L.; Scilimati, A. Synthesis of 3-aryl4,5-dihydro-5-hydroxy-1,2-oxazoles by reaction of substituted benzonitrile oxides with the enolate ion of acetaldehyde. *Tetrahedron* 1987, 43, 2181-2189.

Di'Nunnó, L.; Vitale, P.; Scilimati, A.; Tacconelli, S.; Patrignani, P. Novel synthesis of 3,4-diarylisoxazole analogues of valdecoxib: reversal COX-2 selectivity by sulfonamide group removal. *J Med Chem.* 2004, 47, 4881-4890.

Isoxazole derivatives and their use as cyclooxygenase inhibitors" Patrignani, P.; Tacconelli, S.; Porreca, E.; Stuppia, L. PCT Int. 2005, WO2005068442. University of Bari, University of Chieti. Di Nunno, L.; Vitale, P.; Patrignani, P.; Tacconelli, S. Italian Patent Application MI2004A000019, 2004.

A synthesis scheme for 3,4-diarylisoxazoles with general formula (1) is indicated in Scheme 1 below:

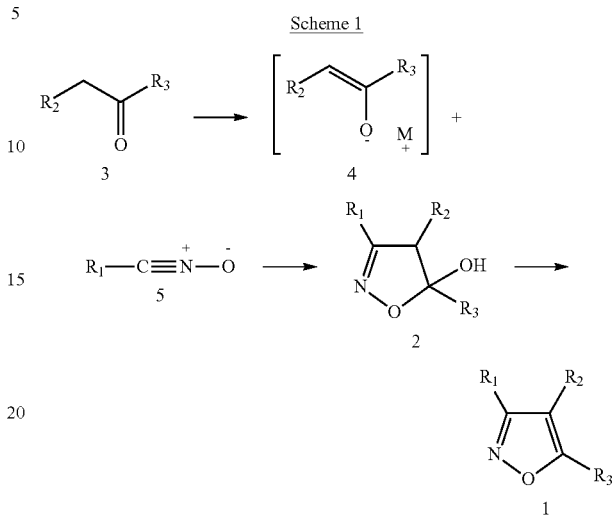

With reference to Scheme 1 above, the desired enolate (4) is prepared starting from the corresponding ketone (3) in the presence of LDA or NaH at the temperature of 0° C. Next, the enolate is reacted with various aryl nitrile oxides (5) to give 5-hydroxy-2-isoxazole compounds (2), where the substituents are defined as indicated above for the same substituents in the compounds with formula (1). These compounds are obtained with good yields and with good diastereoisomeric ratios. In turn, 5-hydroxy-isoxazole compounds (2) according to the invention are then converted into the corresponding isoxazole compounds (1) in basic or acid conditions.

Always according to the present invention, for example the compounds with general formula (1), obtained according to the scheme indicated above, may be advantageously further derivatised/modified or they may also be further subjected to different derivatisation reactions of the substituents $R_1$, $R_2$ and $R_3$ which replace the isoxazole ring.

Always according to the present invention, on the basis of a synthesis scheme similar to scheme 2 indicated above (in which the enolate is replaced by an alkyne and the product obtained from the cycloaddition reaction is already the final diarylisoxazole), it is possible to prepare diarylisoxazole derivatives differently substituted on the isoxazole ring, for example derivatives where the substituent group $R_3$ is in position 4 instead of 5 and the group $R_1$ and/or $R_2$ alternatively in the place of $R_3$ in position 5 instead of position 3 and/or 4.

Always according to the present invention, it has been seen that compounds having the following general formula (1):

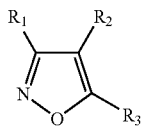 (1)

where the substituents are defined as above, are advantageously used as chemotherapeutic agents, anti-inflammatory agents, analgesics and as drugs suitable for the prevention of cardiovascular diseases (antithrombotics/vasoprotectives/cardioprotectives) and in particular as alternative drugs to acetylsalicylic acid, especially in the treatment of patients who show resistance to acetylsalicylic acid.

In particular, with reference to the compounds with general formula (1), $R_3$ is chosen as $CH_3$, $CH_3CH_2$, $CF_3$, COOH, $COOCH_3$, $COO(CH_2)_3(NOC_4H_8)$ [by $(NOC_4H_8)$ we mean the morpholine group], $COO(CH_2)_3Br$, $COO(CH_2)_3ONO_2$, $CH_2OH$, $CH_2OCOCH_3$.

$R_1$ is chosen among the following substituents:
 (a) phenyl
 (b) 3-chlorophenyl
 (c) 5-halogen-2-furyl
 (d) 5-alkyl-2-furyl
 (e) tetrahydrofuranyl;

$R_2$ is chosen as phenyl, 2- or 4-fluorophenyl.

According to a preferential aspect, $R_3$ is chosen as $CH_3$, $CH_3CH_2$, $CF_3$, COOH, $COOCH_3$, $COO(CH_2)_3(NOC_4H_8)$ [by $(NOC_4H_8)$ we mean the morpholine group], $COO(CH_2)_3Br$, $COO(CH_2)_3ONO_2$, $CH_2OH$, $CH_2OCOCH_3$; $R_1$ is chosen among the following substituents:
 (a) phenyl
 (b) 2-chlorophenyl
 (c) 3-chlorophenyl
 (d) 5-bromo-2-furyl
 (e) 5-chloro-2-furyl
 (f) 5-methyl-2-furyl
 (g) tetrahydrofuranyl;

$R_2$ is chosen as phenyl, 2- or 4-fluorophenyl.

Always according to the present invention, the preferred compounds with general formula (1) are the following:
 compound P10 where: $R_3$ is chosen as methyl ($CH_3$), $R_1$ is chosen as (a) phenyl, $R_2$ is chosen as phenyl;
 compound P9 where: $R_3$ is chosen as ethyl ($CH_3CH_2$), $R_1$ is chosen as (a) phenyl, $R_2$ is chosen as phenyl;
 compound P6 where: $R_3$ is chosen as methyl ($CH_3$), $R_1$ is chosen as (c) 5-chloro-2-furyl, $R_2$ is chosen as phenyl.

The derivatives according to the present invention, with general formula (1), have shown an interesting activity as inhibitors of cyclooxygenase (COX), in particular of cyclooxygenase-1 (COX-1), and therefore an activity as non-steroidal anti-inflammatory drugs (NSAID), but they have also surprisingly shown a significant antithrombotic/vasoprotective/cardioprotective activity, which allows their use as drugs suitable for the prevention of cardiovascular diseases and in particular as alternative drugs to acetylsalicylic acid, especially in the treatment of patients who show resistance to acetylsalicylic acid. Patients who require preventive treatment for the "protection" of the cardiovascular system can therefore be advantageously treated with the compounds according to the invention, as an alternative to treatment with acetylsalicylic acid, especially when they show resistance to the same which prevents, or strongly limits, its cardioprotective action.

Moreover, according to the invention, the compounds with general formula (1) may possibly be administered in association with drugs that inhibit the proton pump or may be variously functionalised to reduce or avoid the onset of any harmful side effects on the gastrointestinal apparatus.

The compounds according to the invention have also shown a reduced renal toxicity, a high analgesic, anti-inflammatory and chemopreventive activity, and are thus advantageously used as drugs protecting the cardiovascular apparatus and in the prevention of the onset of cardiovascular pathologies such as thrombosis and atherosclerosis.

As a non-limiting example of the present invention, below are given some examples of the preparation of the compounds according to the invention.

General Procedure for the Synthesis of 3-aryl-5-hydroxy-5-alkyl-4-aryl-2-isoxazolines with General Formula (2) by Reaction of Enolate Ions of 3-aryl-2-propanones and Aryl Nitrile Oxides A solution of the appropriate 3-aryl-2-propanone (4.5 mmoles) in THF (20 ml) is slowly added to a suspension of 95% NaH w/w (7.2 mmoles) in THF (45 ml) kept stirring at 0° C. and in an atmosphere of $N_2$. The reaction mixture is kept stirring for 1 hour at 0° C. before adding aryl nitrile oxide (4.5 mmoles) solubilised in THF (35 ml). The reaction mixture is then brought to ambient temperature and the reaction is blocked after 12 h by adding a saturated aqueous solution of $NH_4Cl$. The two phases are separated and the aqueous phase is extracted three times with ethyl acetate. The combined organic extracts are dried over $Na_2SO_4$ and the solvent distilled in a vacuum. The residue, composed of 3-aryl-5-hydroxy-5-alkyl-4-aryl-2-isoxazolines with general formula (2) and diarylisoxazoles with general formula (1), subjected to silica gel column chromatography gives (2) with a yield of 56-71% and (1) with a yield of 30-40%. The 3-(2-Chlorophenyl)-4-(2-fluorophenyl)-5-methylisoxazole (example 8) and 3-(2-chlorophenyl)-4-phenyl-5-methylisoxazole (example 9) were obtained, respectively, with a yield of 69 and 78%, by dehydration/aromatisation in situ of the corresponding 3-aryl-5-hydroxy-5-alkyl4-aryl-2-isoxazolines.

EXAMPLE 1

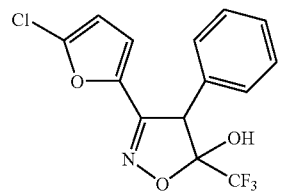

3-(5-Chlorofuran-2-yl)-4-phenyl-5-hydroxy-5-(trifluoromethyl)-2-isoxazoline

Reagents: 1,1,1-Trifluoro-3-phenyl-2-propanone and 2-(5-chlorofuryl)carbonitrile oxide. The product (71% yield) is isolated by chromatography (petroleum ether/ethyl acetate=15:1 until elution of the impurity with larger $R_f$ and then 10:1). FT-IR (neat): 3600-3150, 3037, 2924, 2852, 1616, 1494, 1457, 1324, 1244, 1174, 1086, 1041, 1018, 946, 857, 790, 701 cm$^{-1}$. $^1$H NMR (500 MHz, CDCl$_3$, δ): 7.45-7.43 (m, 3H, aromatic protons, cis diastereoisomer); 7.34-7.32 (m, 3H, aromatic protons, trans diastereoisomer); 7.27-7.24 (m, 4H, two aromatic protons for each diastereoisomer); 6.44 (d, J=3.6 Hz, 1H, furyl proton, trans diastereoisomer); 6.23 (d, J=3.6 Hz, 1H, furyl proton, cis diastereoisomer); 6.16 (d, J=3.6 Hz, 1H, furyl proton, trans diastereoisomer); 6.13 (d, J=3.6 Hz, 1H, furyl proton, cis diastereoisomer); 4.92 (s, 1H, proton of the isoxazoline ring of the cis diastereoisomer); 4.79 (s, 1H, proton of the isoxazoline ring of the trans diastereoisomer); 3.42-3.30 (bs, 2H, OH: exchange with D$_2$O; one proton for each diastereoisomer). $^{13}$C NMR (75 MHz, CDCl$_3$, δ): 150.5, 142.6, 140.4, 129.9, 129.7, 129.5, 129.4, 129.3, 129.1, 122.3 (q, J=287.0 Hz), 116.8, 116.6, 108.9, 108.8, 103.9 (q, J=33.5 Hz), 63.1, 57.7. GC-MS (70 eV) m/z (rel.int.): 333 [(M$^+$+2), 34], 332 [(M$^+$+1), 16], 331 (M$^+$+92), 216 (16), 188 (29), 182 (13), 155 (18), 154 (100), 139 (14), 127 (17), 102 (13), 91 (13), 89 (16), 77 (11), 63 (9), 51 (5). Anal. Calc. for C$_{14}$H$_9$ClF$_3$NO$_3$: C, 50.70; H, 2.73; N, 4.22. Found: C, 50.71; H, 2.77; N, 4.21.

EXAMPLE 2

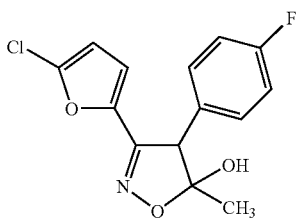

3-(5-Chlorofuran-2-yl)-4-(4-fluorophenyl)-5-hydroxy-5-methyl-2-isoxazoline

Reagents: 3-(4-fluorophenyl)-2-propanone and 2-(5-chlorofuryl)carbonitrile oxide. The product (62% yield) is isolated by chromatography (petroleum ether/ethyl acetate=7:3). M.p. 101-102° C. FT-IR (KBr): 3580-3100, 3050, 2999, 2926, 1602, 1512, 1495, 1442, 1392, 1374, 1318, 1233, 1126, 1014, 945, 917, 898, 828, 786 cm$^{-1}$. $^1$H NMR (300 MHz, CDCl$_3$, δ): 7.30-7.00 (m, 8H, four aromatic protons for each diastereoisomer); 6.47 (d, J=3.5 Hz, 1H, furyl proton, cis diastereoisomer); 6.15 (d, J=3.5 Hz, 1H, furyl proton, cis diastereoisomer); 6.12 (d, J=3.5 Hz, 1H, furyl proton, trans diastereoisomer); 6.09 (d, J=3.5 Hz, 1H, furyl proton, trans diastereoisomer); 4.40 (s, 1H, proton of the isoxazoline ring of the cis diastereoisomer); 4.36 (s, 1H, proton of the isoxazoline ring of the trans diastereoisomer); 1.75 (s, 3H, methyl of the trans diastereoisomer); 1.28 (s, 3H, methyl of the cis diastereoisomer). $^{13}$C NMR (75 MHz, CDCl$_3$, δ): 152.2, 143.3, 131.7, 131.5, 115.9, 115.7, 115.6, 115.0, 108.4, 107.9, 62.0, 49.9, 11.1. GC-MS (70 eV) m/z (rel.int.): 297 (M$^+$+2, 7), 295 (M$^+$, 18), 237 (12), 236 (21), 235 (25), 234 (13), 206 (13), 200 (13), 173 (19), 172 (100), 157 (11), 145 (11), 120 (12), 109 (11), 107 (12), 43 (17). Anal. Calc. for C$_{14}$H$_{11}$ClFNO$_2$: C, 56.87; H, 3.75; N, 4.74. Found: C, 56.80; H, 3.74; N, 4.71.

EXAMPLE 3

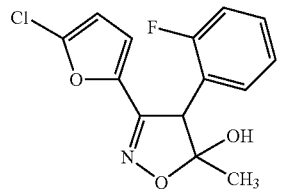

3-(5-Chlorofuran-2-yl)-4-(2-fluorophenyl)-5-hydroxy-5-methyl-2-isoxazoline

Reagents: 3-(2-fluorophenyl)-2-propanone and 2-(5-chlorofuryl)carbonitrile oxide. The product (56% yield) is isolated by chromatography (petroleum ether/ethyl acetate=7:3). M.p. 130-131° C. (mixture of diastereoisomers). FT-IR (KBr): 3590-3200, 3131, 2964, 1613, 1582, 1547, 1490, 1458, 1387, 1378, 1229, 1206, 1145, 1100, 1015, 915, 901, 789, 758 cm$^{-1}$. $^1$H NMR (300 MHz, CDCl$_3$, δ): 7.40-6.90 (m, 8H, four aromatic protons for each diastereoisomer); 6.51 (d, J=3.6 Hz, 1H, furyl proton, cis diastereoisomer); 6.17 (d, J=3.6 Hz, 2H, one furyl proton of cis diastereoisomer and one of trans diastereoisomer); 6.12 (d, J=3.6 Hz, 1H, furyl proton, trans diastereoisomer); 4.84 (s, 2H, protons of the isoxazoline ring, 1H for each diastereoisomer); 3.36 (bs, 1H, OH: exchange with D$_2$O; proton of cis diastereoisomer); 3.15-2.80 (bs, 1H, OH: exchange with D$_2$O, proton of trans diastereoisomer); 1.78 (s, 3H, CH$_3$ trans diastereoisomer); 1.33 (s, 3H, CH$_3$ cis diastereoisomer). $^{13}$C NMR (75 MHz, CDCl$_3$, δ): 160.5 (d, J=247.4 Hz), 152.0, 143.9, 143.7, 139.8, 139.7, 131.3, 130.7 (d, J=8.3 Hz), 130.4 (d, J=8.3 Hz), 129.2, 125.2 (d, J=3.8 Hz), 124.8, 121.4 (d, J=14.5 Hz), 116.0 (d, J=22.0 Hz), 115.5, 115.0, 108.9 (d, J=24.7 Hz), 108.4 (d, J=16.9 Hz), 66.2, 54.6, 25.7, 21.4. GC-MS (70 eV) m/z (rel.int.): 297 (M$^+$+2, 10), 295 (M$^+$, 26), 278 (22), 253 (20), 237 (11), 236 (19), 235 (22), 234 (13), 209 (12), 206 (15), 200 (12), 173 (19), 172 (100), 157 (13), 145 (13), 133 (10), 120 (11), 109 (13), 107 (13), 43 (25). Anal. Calc. for C$_{14}$H$_{11}$ClFNO$_2$: C, 56.87; H, 3.75; N, 4.74. Found: C, 56.84; H, 3.72; N, 4.75.

EXAMPLE 4

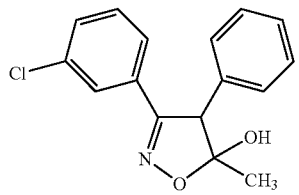

3-(3-Chlorophenyl)-4-phenyl-5-hydroxy-5-methyl-2-isoxazoline

Reagents: phenyl-2-propanone and 3-chlorobenzonitrile oxide The product (71% yield) is isolated by chromatography (petroleum ether/ethyl acetate=10:1 until elution of the impurity with larger R$_f$ and then 8:1). M.p. 124.5-128.4° C. (mixture of diastereoisomers). FT-IR (KBr): 3600-3150, 3078, 3026, 3005, 2987, 2940, 1591, 1561, 1490, 1455, 1409, 1383, 1355, 1339, 1265, 1229, 1139, 1094, 1044, 925, 887, 873, 809, 802, 750, 700, 679 cm$^{-1}$. $^1$H NMR (300 MHz, CDCl$_3$, δ): 7.80-7.77 (m, 1H, aromatic proton, trans diastereoisomer); 7.67-7.64 (m, 1H, aromatic proton, cis diastereoisomer); 7.43-7.01 (m, 16H, aromatic protons, eight protons for each diastereoisomer); 4.50 (s, 1H, proton of the isoxazoline ring of the cis diastereoisomer); 4.40 (s, 1H, proton of the isoxazoline ring of the trans diastereoisomer); 3.35-3.26 (bs, 1H, OH: exchange with D$_2$O; one proton for the cis diastereoisomer); 2.30-2.10 (bs, 1H, OH: exchange with D$_2$O, one proton for the trans diastereoisomer); 1.77 (s, 3H, CH$_3$ of the trans diastereoisomer); 1.27 (s, 3H, CH$_3$ of the cis diastereoisomer). $^{13}$C NMR (75 MHz, CDCl$_3$, δ): 159.87, 134.88, 134.33, 130.94, 130.39, 130.23, 130.12, 130.04, 129.76, 129.58, 129.25, 128.56, 127.40, 127.12, 125.69, 125.38, 63.03, 60.75, 22.39. GC-MS (70 eV) m/z (rel.int.): 287 (M$^+$, 0.7), 269 (18), 229 (35), 228 (26), 227 (100), 226 (9), 193 (9), 192 (15), 165 (23), 137 (17), 134 (9), 116 (15), 91 (17), 90 (30), 89 (34), 77 (9), 75 (12), 43 (26). Anal. Calc. for C$_{16}$H$_{14}$ClNO$_2$: C, 66.79; H, 4.90; N, 4.87. Found: C, 66.76; H, 4.92; N, 4.86.

General Procedure for the Synthesis of Diarylisoxazoles with Formula (1)

To a solution of Na$_2$CO$_3$ (7 mmoles) in water (30 ml) was added 5-alkyl-3,4-diaryl-5-hydroxy-2-isossazoline (3 mmoles) in MeOH (25 ml). The reaction mixture was heated under reflux conditions for 2 h. Then the MeOH was distilled at reduced pressure and ethyl acetate was added. The two phases were separated and the aqueous phase was extracted three times with ethyl acetate. The combined organic phases were dried over anhydrous Na$_2$SO$_4$ and the solvent evaporated at reduced pressure to give the crude isoxazole. By means of chromatography on silica gel (eluent: petroleum ether/ethyl acetate=20:1) the product is isolated (yield 60÷>95%).

EXAMPLE 5

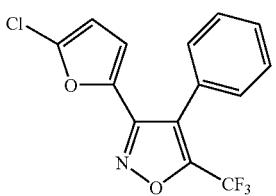

3-(5-Chlorofuran-2-yl)-4-phenyl-5-(trifluoromethyl) isoxazole

Prepared by dehydration/aromatisation of 3-(5-chlorofuran-2-yl)-4-phenyl-5-hydroxy-5-(trifluoromethyl)-2-isoxazoline. Chromatography (eluent: petroleum ether/ethyl acetate=20:1) of the crude reaction product supplied the product with a yield of 65%. M.p. 55-57° C. FT-IR (neat): 3147, 3064, 2925, 2853, 1608, 1517, 1493, 1446, 1415, 1355, 1315, 1260, 1210, 1196, 1160, 1148, 1073, 1023, 992, 968, 943, 899, 775, 756, 700 cm$^{-1}$. $^1$H NMR (300 MHz, CDCl$_3$, δ): 7.51-7.48 (m, 3H, aromatic protons); 7.34-7.32 (m, 2H, aromatic protons); 6.17 (d, J=3.5 Hz, 1H, furyl proton); 6.15 (d, J=3.5 Hz, 1H, furyl proton). $^{13}$C NMR (75 MHz, CDCl$_3$, δ): 155.0 (q, J=40.4 Hz), 153.6, 141.8, 139.9, 129.9, 129.1, 125.9, 118.3 (q, J=272.0 Hz), 115.5, 108.5. GC-MS (70 eV) m/z (rel.int.): 315 [(M$^+$+2), 37], 313 (M$^+$, 100), 250 (13), 244 (15), 216 (22), 190 (23), 189 (11), 188 (64), 153 (22), 152 (19), 129 (20), 127 (12), 89 (20), 77 (6), 73 (10). Anal. Calc. for C$_{14}$H$_7$ClF$_3$NO$_2$: C, 53.61; H, 2.45; N, 4.46. Found: C, 53.60; H, 2.47; N, 4.41.

EXAMPLE 6

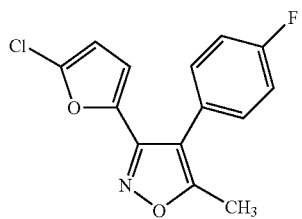

3-(5-Chlorofuran-2-yl)-4-(4-fluorophenyl)-5-methyl-isoxazole

Prepared by dehydration/aromatisation of 3-(5-chlorofuran-2-yl)-4-(4-fluorophenyl)-5-hydroxy-5-methyl-2-isoxazoline. 89% yield. M.p. 103.7-105.2° C. FT-IR (KBr): 3147, 3077, 2931, 1637, 1595, 1522, 1508, 1445, 1418, 1403, 1236, 1230, 1223, 1203, 1158, 1135, 1018, 987, 939, 921, 896, 846, 794 cm$^{-1}$. $^1$H NMR (500 MHz, CDCl$_3$, δ): 7.28-7.26 (m, 2H, aromatic protons); 7.16-7.13 (m, 2H, aromatic protons); 6.29 (d, J=3.5 Hz, 1H, furyl proton); 6.15 (d, J=3.5 Hz, 1H, furyl proton); 2.37 (s, 3H, CH$_3$). $^{13}$C NMR (75 MHz, CDCl$_3$, δ): 167.0, 163.6, 161.7, 152.2, 143.4, 138.5, 131.8, 131.7, 125.3, 125.3, 116.0, 115.8, 113.8, 113.5, 107.9, 11.2. GC-MS (70 eV) m/z (rel.int.): 279 (M$^+$+2, 16), 277 (M$^+$, 49), 237 (35), 236 (19), 235 (100), 234 (12), 206 (12), 172 (46), 171 (20), 170 (11), 147 (16), 145 (20), 89 (13), 43 (30). Anal. Calc. for C$_{14}$H$_9$ClFNO$_2$: C, 60.56; H, 3.27; N, 5.04. Found: C, 60.58; H, 3.24; N, 5.01.

EXAMPLE 7

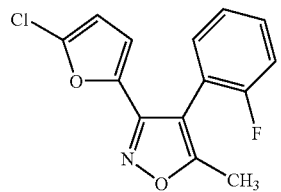

3-(5-Chlorofuran-2-yl)-4-(2-fluorophenyl)-5-methyl-isoxazole

Prepared by dehydration/aromatisation of 3-(5-chlorofuran-2-yl)-4-(2-fluorophenyl)-5-hydroxy-5-methyl-2-isoxazoline. Chromatography (eluent:petroleum ether/ethyl acetate=20:1) of the crude reaction product supplied the oily product with 90% yield. FT-IR (neat): 3144, 3067, 2928, 2854, 1639, 1604, 1580, 1521, 1495, 1455, 1436, 1417, 1208, 1137, 1108, 1021, 989, 943, 923, 899, 789, 763 cm$^{-1}$. $^1$H NMR (400 MHz, CDCl$_3$, δ): 7.43-7.37 (m, 1H, aromatic proton); 7.27-7.14 (m, 3H, aromatic proton); 6.31 (d, J=3.6

Hz, 1H, furyl proton); 6.13 (d, J=3.6 Hz, 1H, furyl proton); 2.34 (s, 3H, CH$_3$). $^{13}$C NMR (100 MHz, CDCl$_3$, δ): 167.8, 160.2 (d, $^1J_{19F-13C}$=247.9 Hz), 152.4, 143.3, 138.3, 132.1 (d, $^4J_{19F-13C}$=2.7 Hz), 130.6 (d, $^3J_{19F-13C}$=8.0 Hz), 124.3 (d, $^4J_{19F-13C}$=3.8 Hz), 117.0 (d, $^2J_{19F-13C}$=16.0 Hz), 115.9 (d, $^2J_{19F-13C}$=21.7 Hz), 113.0, 108.3, 107.9, 11.2 (d, $^5J_{19F-13C}$= 0.8 Hz). GC-MS (70 eV) m/z (rel.int.): 279 [(M$^+$+2), 21], 277 (M$^+$, 57), 237 (36), 236 (20), 235 (100), 234 (14), 206 (11), 172 (49), 171 (18), 145 (19), 43 (15). Anal. Calc. for C$_{14}$H$_9$ClFNO$_2$: C, 60.56; H, 3.27; N, 5.04. Found: C, 60.60; H, 3.30; N, 5.06.

EXAMPLE 8

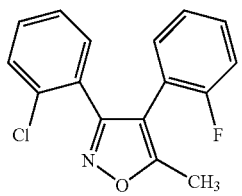

3-(2-Chlorophenyl)-4-(2-fluorophenyl)-5-methyl-isoxazole

Prepared according to the general procedure of compounds with formula (2). The product was isolated with 72% yield in the form of a colourless semi-solid. FT-IR (KBr): 3059, 3033, 2953, 2924, 2852, 1630, 1607, 1579, 1516, 1492, 1437, 1414, 1376, 1315, 1268, 1240, 1212, 1159, 1136, 1105, 1059, 1018, 965, 904, 818, 764, 753, 745, 734, 796, 664 cm$^{-1}$. $^1$H NMR (400 MHz, CDCl$_3$, δ): 7.44-7.41 (m, 1H, aromatic proton); 7.35-7.24 (m, 4H, aromatic protons); 7.09-6.93 (m, 3H, aromatic protons); 2.48 (d, 3H, J=1.5 Hz). $^{13}$C NMR (100 MHz, CDCl$_3$, δ): 167.3, 161.0, 158.5, 133.5, 131.6, 131.1 (d, J=3.0 Hz), 130.7, 129.8, 129.7 (d, J=8.4 Hz), 128.5, 126.7, 124.1 (d, J=3.8 Hz), 117.8 (d, J=15.6 Hz), 115.8 (d, J=22.1 Hz), 111.5, 11.9 (d, J=3.4 Hz). GC-MS (70 eV) m/z (rel.int.): 289 [(M$^+$+ 2), 24], 287 (M$^+$, 69), 272 (13), 247 (34), 246 (20), 245 (100), 244 (14), 210 (7), 208 (9), 183 (14), 107 (34), 75 (6), 43 (8). Anal. Calc. for C$_{16}$H$_{11}$ClFNO: C, 66.79; H, 3.85; N, 4.87. Found: C, 66.98; H, 4.00; N, 5.00.

EXAMPLE 9

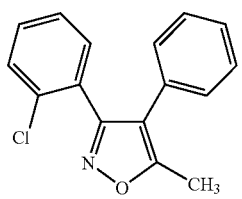

3-(2-Chlorophenyl)-4-phenyl-5-methylisoxazole
[Croitoru, M. et al. *Rev. Chem.* (Bucarest) 2006, 57 (10), 1047-1050]

Prepared according to the general procedure of compounds with formula (2). Obtained in the form of oil, with 78% yield. FT-IR (KBr): 3079, 3065, 3028, 2920, 1633, 1598, 1570, 1494, 1453, 1426, 1397, 1370, 1299, 1234, 1178, 1132, 1091, 1074, 1042, 1018, 975, 914, 897, 790, 757, 688 cm$^{-1}$. $^1$H NMR (400 MHz, CDCl$_3$, δ): 7.42-7.25 (m, 7H, aromatic protons); 7.09-7.06 (m, 2H, aromatic protons); 2.55 (s, 3H). $^{13}$C NMR (100 MHz, CDCl$_3$, δ): 165.8, 160.6, 133.8, 131.7, 130.7, 130.1, 129.9, 128.8, 128.6, 127.3, 126.7, 117.1, 11.80. GC-MS (70 eV) m/z (rel.int.): 271 [(M$^+$+2), 32], 269 (M$^+$, 93), 254 (28), 229 (34), 228 (21), 227 (100), 226 (21), 192 (9), 191 (9), 190 (14), 165 (19), 103 (9), 89 (41), 75 (7), 63 (8), 43 (9). Anal. Calc. for C$_{16}$H$_{12}$ClNO: C, 71.25; H, 4.48; N, 5.19. Found: C, 70.98; H, 4.60; N, 5.20.

EXAMPLE 10

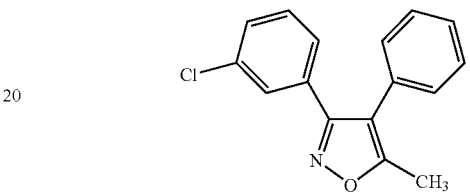

3-(3-Chlorophenyl)-4-phenyl-5-methylisoxazole

BF$_3$Et$_2$O (0.41 mmoles) is added to [3-(3-chlorophenyl)-4-phenyl-5-hydroxy-5-methyl-2-isoxazoline (107 mg, 0.373 mmoles) solubilised in CH$_2$Cl$_2$ (3 ml). The reaction mixture is kept stirring at ambient temperature for 2 h. The reaction is blocked by adding H$_2$O. It is extracted with CH$_2$Cl$_2$. The combined extracts are dried with anhydrous Na$_2$SO$_4$, filtered and concentrated at reduced pressure. The residue is crystallised with hexane (71% yield). FT-IR (KBr): 3079, 3065, 3028, 2921, 1633, 1598, 1570, 1494, 1453, 1426, 1397, 1370, 1299, 1234, 1178, 1132, 1091, 1074, 1042, 1018, 975, 914, 897, 790, 757, 688 cm$^{-1}$. $^1$H NMR (300 MHz, CDCl$_3$, δ): 7.52-7.48 (m, 1H, aromatic proton); 7.44-7.30 (m, 4H, aromatic protons); 7.28-7.14 (m, 4H, aromatic protons); 2.45 (s, 3H, CH$_3$). $^{13}$C NMR (75 MHz, CDCl$_3$, δ): 167.2, 160.2, 134.7, 131.1, 130.1, 130.0, 129.9, 129.7, 129.1, 128.6, 128.1, 126.8, 116.0, 11.8. GC-MS (70 eV) m/z (rel.int.): 271 [(M$^+$+ 2), 37], 270 [(M$^+$+1), 21], 269 (M$^+$, 100), 256 (9), 254 (25), 229 (35), 228 (23), 227 (97), 226 (20), 191 (9), 190 (11), 165 (21), 103 (14), 89 (41), 77 (8), 75 (11), 63 (12), 43 (19). Anal. Calc. for C$_{16}$H$_{12}$ClNO: C, 71.25; H, 4.48; N, 5.19. Found: C, 71.21; H, 4.47; N, 5.21.

EXAMPLE 11

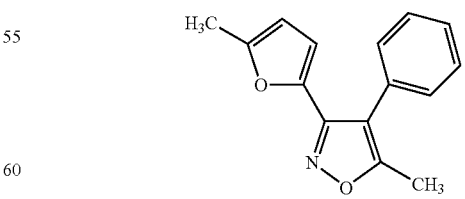

4-Phenyl-5-methyl-3-(5-methylfuran-2-yl)isoxazole.

Prepared with 60% yield by dehydration/aromatisation of 3-(5-methylfuran-2-yl)-4-phenyl-5-hydroxy-5-methyl-2- isoxazoline. 60% yield. Yellow oil. FT-IR (KBr): 3058, 2924, 2852, 1627, 1598, 1566, 1498, 1435, 1239, 1208, 1149, 1074, 1024, 922, 898, 791, 772, 701 cm$^{-1}$. $^1$H NMR (400 MHz, CDCl$_3$, δ): 7.44-7.40 (m, 3H, aromatic protons); 7.31-7.24 (m, 2H, aromatic protons); 6.12 (d, 1H, J=3.3 Hz, furyl protons); 5.94-5.92 (m, 1H, furyl protons); 2.36 (s, 3H); 2.32 (s, 3H). $^{13}$C NMR (100 MHz, CDCl$_3$, δ): 166.3, 153.9, 153.0, 142.2, 130.1, 130.0, 128.6, 128.1, 112.8, 107.3, 13.6, 11.2. GC-MS (70 eV) m/z (int. rel.): 239 (M$^+$, 48), 198 (15), 197 (100), 196 (23), 168 (5), 167 (6), 154 (7), 129 (7), 127 (5), 115 (5), 89 (4), 43 (7). 102 (10), 261 (100), 234 (10), 232 (10), 154 (54), 153 (33), 129 (12), 127 (31), 77 (9), 43 (14). Anal. Calc. for C$_{15}$H$_{13}$NO$_2$: C, 75.30; H, 5.48; N, 5.85. Found: C, 75.08; H, 5.60; N, 5.90.

Scheme 3

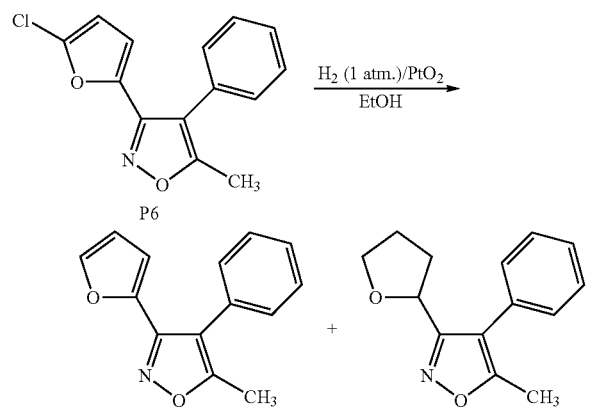

EXAMPLE 12

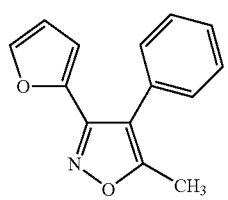

3-(Furan-2-yl)-4-phenyl-5-methylisoxazole

A solution of EtOH (2 ml) containing 3-(5-chlorofuran-2-yl)-4-phenyl-5-methylisoxazole (97 mg, 0.374 mmoles), PtO$_2$ (5 mg) is kept in an atmosphere of H$_2$ (1 atm) at ambient temperature, stirring for 7 h. The catalyst is then filtered on celite and the solvent is evaporated at reduced pressure. The residue is crystallised from hexane. A white powder is obtained with 89% yield and a m.p. 93-96° C. (hexane). FT-IR (KBr): 3149, 3122, 3059, 2962, 2925, 2853, 1633, 1605, 1511, 1496, 1448, 1438, 1417, 1239, 1225, 1176, 1070, 1020, 976, 923, 891, 782, 714, 700 cm$^{-1}$. $^1$H NMR (400 MHz, CDCl$_3$, δ): 7.47-7.41 (m, 4H, aromatic protons); 7.31-7.28 (m, 2H, aromatic protons); 6.37-6.35 (dd, 1H, J=3.3 Hz, J=1.8 Hz, furyl proton); 6.34-6.33 (d, 1H, J=3.3 Hz, furyl proton); 2.39 (s, 3H). $^{13}$C NMR (100 MHz, CDCl$_3$, δ): 166.6, 153.1, 144.0, 143.6, 130.0, 129.8, 128.7, 128.1, 114.9, 111.5, 111.1, 11.2. GC-MS (70 eV) m/z (rel.int.): 225 (M$^+$, 40), 184 (14), 183 (100), 154 (17), 127 (13), 102 (12), 43 (11). Anal. Calc. for C$_{14}$H$_{11}$NO$_2$: C, 74.65; H, 4.92; N, 6.22; O, 14.21. Found: C, 74.48; H, 4.94; N, 6.19.

EXAMPLE 13

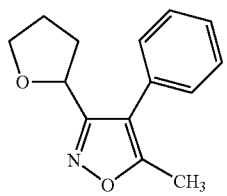

4-Phenyl-5-methyl-3-(tetrahydrofuran-2-yl)isoxazole

Preparation is carried out in the same conditions as the previous example [3-(furan-2-yl)-4-phenyl-5-methylisoxazole], the difference is in the duration of the reaction which in this case is 14 h. A colourless semi-solid is obtained with 22% yield. FT-IR (neat): 3058, 2924, 2852, 1629, 1600, 1500, 1444, 1237, 1057, 1012, 920, 771, 701 cm$^{-1}$. $^1$H NMR (500 MHz, CDCl$_3$, δ): 7.44-7.41 (m, 2H, aromatic protons); 7.37-7.34 (m, 3H, aromatic protons); 4.97 (t, 1H, J=6.9 Hz); 3.91-3.83 (m, 2H); 2.39 (s, 3H); 2.22-2.08 (m, 2H); 2.05-185 (m, 2H). $^{13}$C NMR (125 MHz, CDCl$_3$, δ): 166.1, 162.6, 130.0, 129.7, 128.6, 127.6, 116.2, 72.7, 68.4, 30.2, 26.0, 11.4. GC-MS (70 eV) m/z (rel.int.): 229 (M$^+$, 12), 186 (6), 173 (6), 158 (4), 117 (10), 115 (6), 103 (7), 89 (9), 77 (5), 71 (100), 63 (4), 51 (5), 43 (30), 41 (9). Anal. Calc. for C$_{14}$H$_{15}$NO$_2$: C, 73.34; H. 6.59; N, 6.11. Found: C, 73.48; H, 6.60; N, 6.10.

EXAMPLE 14

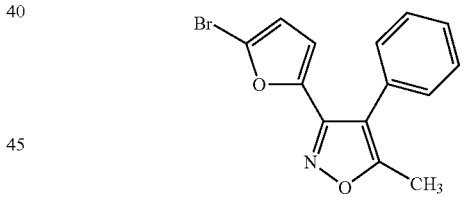

3-(5-Bromofuran-2-yl)-4-phenyl-5-methylisoxazole

To a solution of 3-(furan-2-yl)-4-phenyl-5-methylisoxazole (0.152 g, 0.670 mmol) in anhydrous DMF (6 ml), kept stirring at 0° C., is slowly added NBS (0.144 g, 0.810 mmol). A suspension is formed which is kept stirring for 2 h at ambient temperature. Water is then added, and then ethyl acetate. The two phases are separated and the aqueous phase is extracted three times with ethyl acetate. The total organic phase is first washed with a saline aqueous solution (NaCl) and then dried with anhydrous Na$_2$SO$_4$. The solvent is evaporated at reduced pressure. A yellow solid is obtained. When subjected to chromatography (silica gel, petroleum ether/ethyl acetate=9:1) it gave the product with 60% yield, as a white solid; m.p. 93-96° C. (hexane). FT-IR (KBr): 3143, 3055, 2962, 2923, 2851, 1632, 1605, 1505, 1434, 1408, 1236, 1202, 1122, 1019, 984, 921, 896, 796, 774, 721, 704, 676, 561 cm$^{-1}$. $^1$H NMR (400 MHz, CDCl$_3$, δ): 7.44-7.35 (m, 3H, aromatic protons); 7.26-7.23 (m, 2H, aromatic protons); 6.24 (d, 1H, J=3.3 Hz, furyl proton); 6.20 (d, 1H, J=3.3 Hz, furyl proton); 2.34 (s, 3H). $^{13}$C NMR (100 MHz, CDCl$_3$, δ): 166.7, 152.1, 145.8, 129.9, 129.3, 128.7, 128.3, 124.1, 114.6, 113.8, 112.9, 11.1. GC-MS (70 eV) m/z (rel.int.): 305 [(M$^+$+2), 47], 303 (M$^+$, 100), 264 (13), 263 (98), 262 (23), 261 (100), 234 (10), 232 (10), 154 (54), 153 (33), 129 (12), 127 (31), 77 (9), 43 (14). Anal. Calc. For C$_{14}$H$_{10}$BrNO$_2$: C, 55.29; H, 3.31; N, 4.61. Found: C, 55.08; H, 3.60; N, 4.20.

Scheme 4

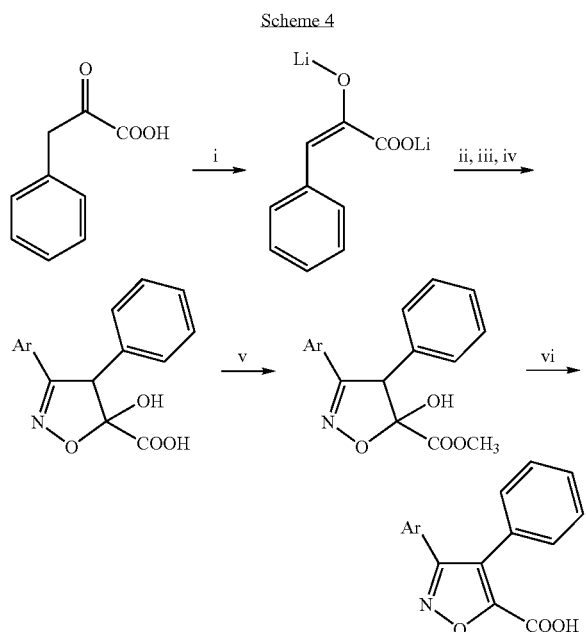

Reagents and conditions: (i) 2 eq. LDA, THF, 1 hour, 0° C.; (ii) ArCNO, THF, 16 THF, 16 hours; (iii)sat. NH$_4$Cl.; (iv) BF$_3$/MeOH, amb.t., 3 hours; (vi) Na$_2$CO$_3$, MeOH, reflux.

EXAMPLE 15

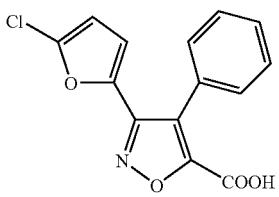

Synthesis of [3-(5chlorofuran-2-yl)-4-phenylisoxazol-5-yl]carboxylic acid n-Butyllithium in hexane (2.25M, 0.54 ml, 1.215 mmoles) is added to diisopropylamine (0.19 ml, 1.215 mmoles) in THF (7 ml) kept stirring at 0° C. and in a nitrogen atmosphere. After 15 minutes, a solution of phenylpiruvic acid (100 mg, 0.6097 mmoli) in THF (3 ml) is added slowly. To the reaction mixture which has become red is added, after 1 h, the solution of 2-(5-chlorofuryl)carbonitrile oxide (0.6097 mmoles) in THF (3 ml). The reaction mixture, brought to ambient temperature, is kept stirring at ambient temperature for 16 h, then blocked by adding 10 ml of a saturate solution of NH$_4$Cl and then HCl 1N until an acid pH. The two phases were separated and the aqueous phase extracted three times with chloroform. The combined organic extracts were dried over Na$_2$SO$_4$, filtered and concentrated in a vacuum. The residue consisting of [3-(5-chlorofuran-2-yl)-4-phenyl-5-hydroxy-2-isoxazolin-5-yl]carboxylic acid (185 mg), treated with ethyl ether is filtered and used without further purification for the preparation of methyl ester. $^1$H NMR (300 MHz, CDCl$_3$, δ): 11.00-10.75 (bs, 2H, COOH: exchange with D$_2$O; one proton for each diastereomer); 7.40-7.21 (m, 10H, aromatic protons, five protons for each diastereomer); 6.41 (d, J=3.6 Hz, 1H, furyl proton, trans diastereoisomer); 6.14 (d, J=3.6 Hz, 1H, furyl proton, trans diastereoisomer); 6.07 (d, J=3.4 Hz, 1H, furyl proton, cis diastereoisomer); 5.98 (d, J=3.4 Hz, 1H, furyl proton, cis diastereoisomer); 5.24 (s, 1H, proton of the isoxazoline ring of the cis diastereoisomer); 4.76 (s, 1H, proton of the isoxazoline ring of the trans diastereoisomer); 3.20-3.00 (bs, 2H, OH: exchange with D$_2$O; one proton for each diastereoisomer). $^{13}$C NMR (75 MHz, CDCl$_3$, δ): 171.4, 150.2, 144.5, 139.0, 133.3, 130.8, 130.5, 129.6, 129.1, 128.7, 128.4, 128.1, 105.8, 46.9. LS-MS (ESI$^-$): 306 [(M−1)$^-$, 39], 117 (100). Anal. Calc. for C$_{14}$H$_{10}$ClNO$_5$: C, 54,65; H, 3.28; N, 4.55. Found: C, 54.69; H, 3.31; N, 4.56.

The [3-(5-chlorofuran-2-yl)-4-phenyl-5-hydroxy-2-isoxazolin-5-yl]carboxylic acid (180 mg, 0.586 mmoles) is mixed at 0° C. with the BF$_3$/MeOH (1.3 M, 0.9 ml, 1.17 mmoles). After 5 minutes the ice bath is removed and the reaction mixture is kept stirring for 3 h at ambient temperature. The MeOH is distilled at a reduced pressure and the product is extracted with ethyl acetate (three times). It is dried with Na$_2$SO$_4$, filtered, and the solvent is distilled at a reduced pressure. 172 mg of crude product are obtained which are subjected to chromatography on silica gel (eluent:petroleum ether/ethyl acetate=8:2). 141 mg of product (75% yield) are obtained methyl [3-(5-chlorofuran-2-yl)-4-phenyl-5-hydroxy-2-isoxazolin-5-yl]carboxylate. M.p. 138.8-142.0° C. FT-IR (KBr): 3650-3130, 3030, 2925, 2849, 1743, 1613, 1490, 1451, 1377, 1207, 1123, 946, 894, 831, 793, 699 cm$^{-1}$. $^1$H NMR (300 MHz, CDCl$_3$, δ): 7.36-7.14 (m, 10H, aromatic protons, five protons for each diastereoisomer); 6.45 (d, J=3.2 Hz, 1H, furyl proton, trans diastereoisomer); 6.16 (d, J=3.2 Hz, 1H, furyl proton, trans diastereoisomer); 6.09 (d, J=3.3 Hz, 1H, furyl proton, cis diastereoisomer); 6.03 (d, J=3.3 Hz, 1H, furyl proton, cis diastereoisomer); 5.21 (s, 1H, proton of the isoxazoline ring of the cis diastereoisomer); 4.78 (s, 1H, proton of the isoxazoline ring of the trans diastereoisomer); 4.60-4.20 (bs, 2H, OH: exchange with D$_2$O; one proton for each diastereoisomer); 3.94 (s, 3H, CH$_3$ of the cis distereoisomer); 3.30 (s, 3H, CH$_3$ of the trans distereoisomer). $^{13}$C NMR (75 MHz, CDCl$_3$, δ): 168.6, 150.5, 143.2, 140.0, 130.8, 130.5, 129.0, 128.9$_6$, 128.9$_1$, 128.8, 128.8, 116.3, 108.8, 108.6, 103.9, 58.9, 54.4. GC-MS (70 eV) m/z (rel.int.): 323 [M($^{37}$Cl)$^+$, 19], 321 [M($^{35}$Cl)$^+$, 47], 262 (16), 219 (9), 218 (10), 217 (16), 216 (20), 188 (15), 182 (12), 155 (20), 154 (100), 153 (9), 140 (10), 139 (25), 135 (62), 128 (12), 127 (25), 118 (19), 115 (11), 107 (23), 102 (17), 91 (22), 90 (23), 89 (29), 79 (22), 77 (24), 73 (12), 64 (11), 63 (15). Anal. Calc. for C$_{15}$H$_{12}$ClNO$_5$: C, 56.00; H, 3.76; N, 4.35. Found: C, 56.09; H, 3.71; N, 4.50.

A solution of Na$_2$CO$_3$ (237 mg, 2.24 mmoles) in water (10 ml) was added to the methyl [3-(chlorofuran-2-yl)-4-phenyl-5-hydroxy-2-isoxazolin-5-yl]carboxylate (360 mg, 1.12 mmoles) in MeOH (10 ml). The reaction mixture was heated under reflux conditions for 2 h. It was then acidified with HCl and then the MeOH was distilled at a reduced pressure and CHCl$_3$ was added. The two phases were separated and the aqueous phase was extracted three times with CHCl$_3$. The combined organic phases were dried over anhydrous Na$_2$SO$_4$ and the solvent evaporated at a reduced pressure to give the crude [3-(5chlorofuran-2-yl)-4-phenylisoxazol-5-yl]carboxylic acid which is purified by crystallisation from CHCl$_3$/hexane (300 mg, 93% yield). M.p. 168-170° C. FT-IR (KBr): 3500-2850, 1709, 1614, 1592, 1521, 1454, 1416, 1392, 1305, 1249, 1208, 1153, 1122, 1022, 1006, 981, 941, 899, 779, 696 cm$^{-1}$. $^1$H NMR (300 MHz, CDCl$_3$, δ): 7.48-7.42 (m, 3H, aromatic protons); 7.39-7.32 (m, 2H, aromatic protons); 7.00-6.50 (bs, 1H, OH: exchange with D$_2$O); 6.14 (d, J=3.6 Hz, 1H, furyl proton); 6.12 (d, J=3.6Hz, 1H, furyl proton). $^{13}$C NMR (75 MHz, CDCl$_3$, δ): 159.9, 154.8, 153.6, 141.6, 139.2, 129.4, 129.1, 128.3, 126.8, 123.9, 114.8, 107.9. LC-MS (ESI$^-$): 288[(M−1)$^-$, 69], 117 (100). Anal. Calc. for C$_{14}$H$_8$ClNO$_4$: C, 58.05; H, 2.78; N, 4.83. Found: C, 58.07; H, 2.75; N, 4.80.

2962, 2924, 2848, 1737, 1610, 1594, 1521, 1491, 1441, 1417, 1347, 1307, 1240, 1215, 1149, 1116, 1031, 1014, 987, 936, 803, 698 cm$^{-1}$. $^1$H NMR (500 MHz, CDCl$_3$, δ): 7.48-7.47 (m, 3H, aromatic protons); 7.35-7.33 (m, 2H, aromatic protons); 6.14 (m, 1H, furyl proton); 6.12 (m, 1H, furyl proton); 3.86 (s, 3H, CH$_3$). $^{13}$C NMR (75 MHz, CDCl$_3$, δ): 157.3, 156.0, 153.9, 142.3, 139.54; 130.0, 129.5, 128.7, 127.7, 123.3, 115.1, 108.4, 52.6. GC-MS (70 eV) m/z (rel.int.): 305 [M($^{37}$Cl)$^+$, 35], 303 [M($^{35}$Cl)$^+$, 100], 249 (12), 247 (36), 246 (21), 244 (29), 240 (21), 232 (20), 218 (13), 216 (30), 212 (49), 190 (28), 189 (14), 188 (84), 180 (17), 153 (57), 152 (51), 145 (19), 129 (25), 128 (16), 127 (29), 126 (12), 115 (10), 91 (19), 89 (96), 77 (24), 75 (16), 73 (13), 63 (27), 59 (10), 51 (11). Anal. Calc. for C$_{15}$H$_{10}$ClNO$_4$: C, 59.32; H, 3.32; N, 4.61. Found: C, 59.69; H, 3.51; N, 4.30.

Scheme 5

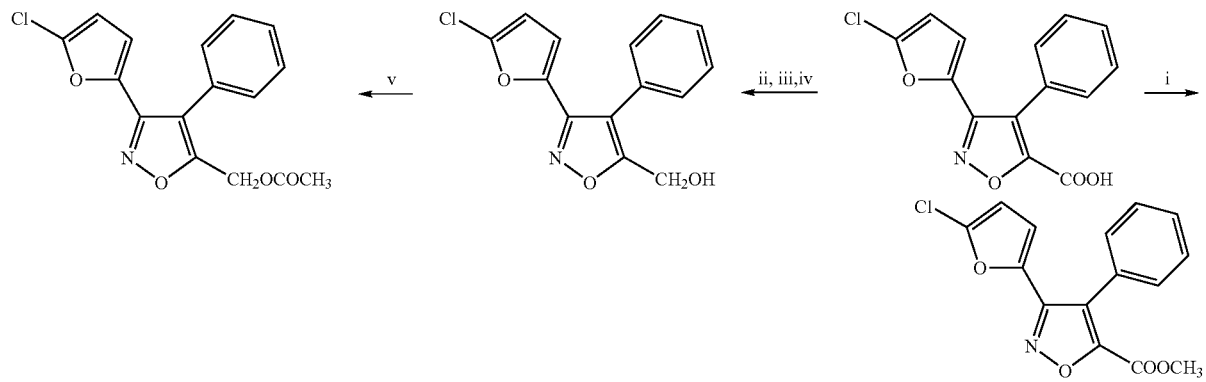

Reagents and conditions: (i) H$_2$SO$_4$, MeOH, amb.t.; (ii) BMS, 5 hours, amb.t.; (iii) H$_2$O (10 mL); (iv) 3N NaOH and H$_2$O$_2$ (30%), 30 min.; (v) Ac$_2$O/Et$_3$N, 0° C. at amb.t., 1.5 hours.

EXAMPLE 16

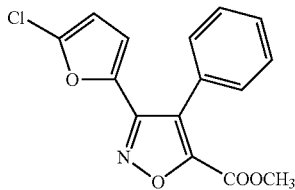

Methyl [3-(5-chlorofuran-2-yl)-4-phenylisoxazol-5-yl]carboxylate

To the solution of [3-(5-chlorofuran-2-yl)-4-phenylisoxazol-5-yl]carboxylic acid (1.119 g, 3.87 mmoles) in CH$_3$OH (28 ml) H$_2$SO$_4$ is slowly added (14 ml). The reaction mixture is kept stirring at ambient temperature for 4 hours. Another ml of H$_2$SO$_4$ is then added. The reaction is blocked after other 2 hours by adding ethyl ether and ice. The two phases are separated and the aqueous phase is extracted three times with ethyl ether. The combined organic extracts are dried over Na$_2$SO$_4$ and the solvent distilled in a vacuum. The residue (1.044 g) subjected to column chromatography (silica gel, petroleum ether/ethyl acetate=10:1) gives 520 mg of product with a yield of 45%. M.p. 130-131° C. FT-IR (KBr): 3135,

EXAMPLE 17

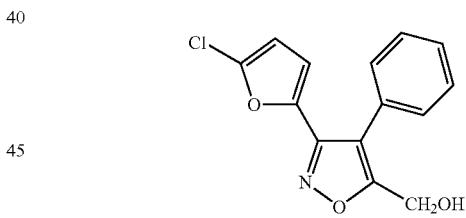

3-(5-Chlorofuran-2-yl)-4-phenyl-5-hydroxymethyl-isoxazole

A 2M solution of the borane-dimethylsulphide complex in THF (1.72 ml, 3.44 mmoles) is added drop wise to the [3-(5-chlorofuran-2-yl)-4-phenylisoxazol-5-yl]carboxylic acid (500 mg, 1.73 mmoles) solubilised in anhydrous THF (6 ml) and kept stirring at 0° C. in an atmosphere of N$_2$. The reaction mixture is brought to ambient temperature and kept stirring. After 15 hours more BMS is added (1.72 ml), and after 9 more hours the reaction is blocked by adding H$_2$O (10 ml), NaOH 3N (10 ml) and H$_2$O$_2$ (30% w/w, 10 ml). The mixture is kept stirring for 30 minutes. The two phases are separated and the aqueous phase is extracted three times with ethyl acetate. The combined organic extracts are dried over Na$_2$SO$_4$ and the solvent distilled in a vacuum. The residue (470 mg) subjected to column chromatography (silica gel, petroleum ether/ethyl acetate=9:1 until 1:1, modified with the elution of the products) gives the product which is crystallised cold from ethyl acetate/hexane (1:1) with a final yield of 52%, the equivalent of 248 mg. M.p. 102-103° C. FT-IR (KBr): 3600-3210, 3144, 3128, 3054, 2927, 1594, 1511, 1447, 1405, 1356, 1289, 1216, 1129, 1019, 1010, 942, 925, 902, 802, 769, 702 cm$^{-1}$. $^1$H NMR (400 MHz, CDCl$_3$, δ): 7.45-7.41 (m, 3H, aromatic protons); 7.35-7.30 (m, 2H, aromatic protons); 6.28 (d, J=3.4 Hz, 1H, furyl proton); 6.12 (d, J=3.4 Hz, 1H, furyl proton); 4.65 (s, 2H, CH$_2$OH); 2.30-2.05 (bs, 1H, OH: exchange with D$_2$O). $^{13}$C NMR (100 MHz, CDCl$_3$, δ): 167.6, 152.5, 143.2, 138.9, 130.2, 129.1, 129.0, 128.5, 116.6, 114.3, 108.2, 54.8. GC-MS (70 eV) m/z (rel.int.): 277 [M($^{37}$Cl)$^+$, 33], 275 [M($^{35}$Cl)$^+$, 100], 246 (12), 244 (32), 238 (14), 218 (14), 217 (16), 216 (32), 212 (29), 211 (31), 190 (21), 188 (58), 183 (10), 182 (11), 180 (10), 154 (42), 153 (38), 152 (35), 129 (18), 128 (14), 127 (25), 91 (14), 89 (42), 77 (13), 63 (11). Anal. Calc. for C$_{14}$H$_{10}$ClNO$_3$: C, 60.99; H. 3.66; N, 5.08. Found: C, 61.00; H, 3.62; N, 5.06.

EXAMPLE 18

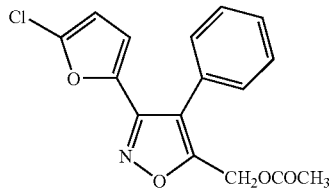

5-Acetoxymethyl-3-(5-chlorofuran-2-yl)-4-phenyl-isoxazole

To a solution of 3-(5-chlorofuran-2-yl)-4-phenyl-5-hydroxymethylisoxazole (350 mg, 1.273 mmoli) in Ac$_2$O (5.2 ml), kept stirring at 0° C., is added Et$_3$N (0.213 ml, 1.531 mmole). The mixture is brought to ambient temperature and kept stirring for 1.5 h. The reaction is blocked by adding ice and 10 ml of saturated solution of NaHCO$_3$. The two phases are separated and the aqueous phase is extracted three times with methylene chloride. The combined organic extracts are dried over Na$_2$SO$_4$ and the solvent distilled in a vacuum. The residue subjected to column chromatography (silica gel, petroleum ether/ethyl acetate=9:1, and 8:2 after the elution of the first substance) gives 237 mg of oily product with a yield of 60%. FT-IR (neat): 3132, 3053, 2921, 1751, 1636, 1517, 1432, 1412, 1372, 1359, 1226, 1127, 1048, 1018, 985, 939, 903, 790, 777, 704 cm$^{-1}$. $^1$H NMR (400 MHz, CDCl$_3$, δ): 7.44-7.42 (m, 3H, aromatic protons); 7.30-7.28 (m, 2H, aromatic protons); 6.24 (d, J=3.6 Hz, 1H, furyl proton); 6.11 (d, J=3.6 Hz, 1H, furyl proton); 5.07 (s, 2H, CH$_2$); 2.02 (s, 3H, CH$_3$).$^{13}$C NMR (75 MHz, CDCl$_3$, δ): 170.3, 163.5, 152.7, 143.1, 139.0, 130.2, 129.2, 129.2, 128.2, 118.2, 114.4, 108.2, 55.4, 20.7. GC-MS (70 eV) m/z (rel.int.): 319 [M($^{37}$Cl)$^+$, 33], 317 [M($^{35}$Cl)$^+$, 90], 277 (18), 276 (10), 275 (49), 240 (18), 238 (10), 217 (23), 216 (11), 213 (17), 212 (100), 211 (32), 190 (11), 188 (27), 182 (11), 154 (20), 153 (26), 152 (21), 129 (15), 127 (19), 91 (12), 89 (26), 73 (11), 43 (30). Anal. Calc. for C$_{16}$H$_{12}$ClNO$_3$: C, 64.48; H, 3.81; N, 4.41. Found: C, 64.46; H, 3.82; N, 4.46.

Scheme 6

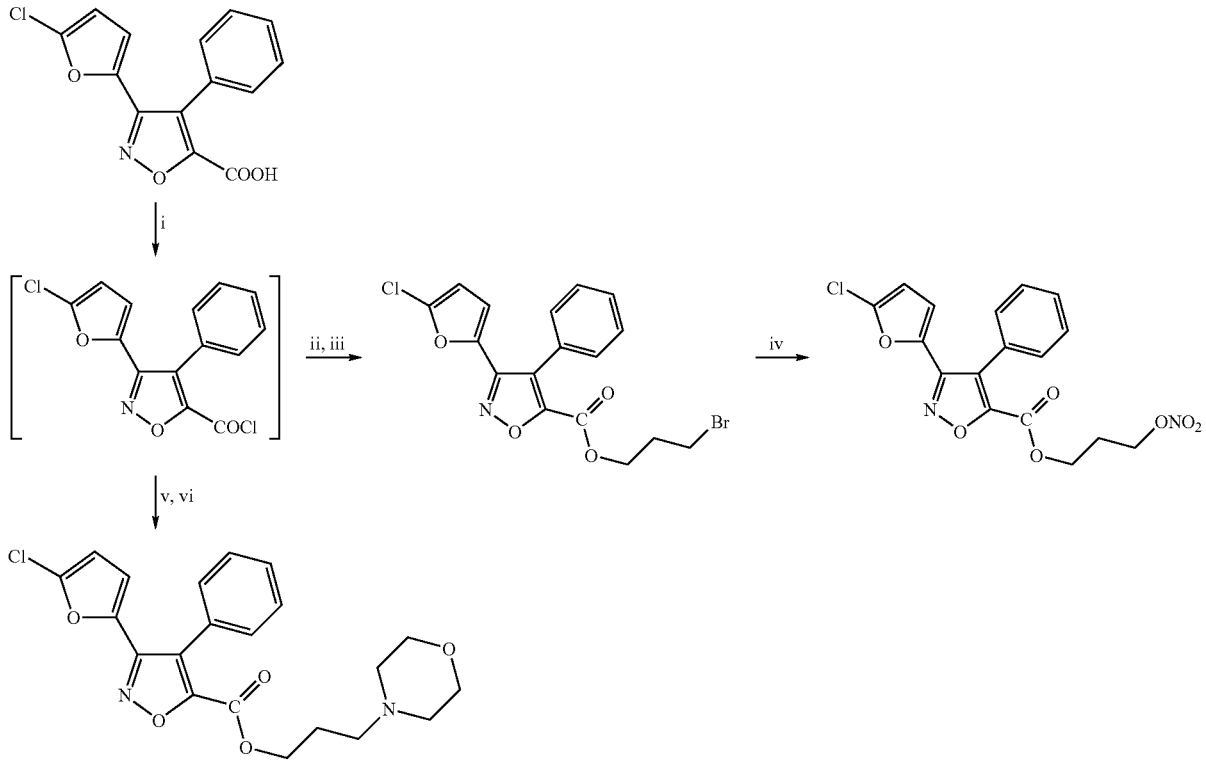

Reagents and conditions: (i) SOCL$_2$, 2 hours, reflux; (ii) Br(CH$_2$)$_3$OH/Et$_3$N, Ch$_2$Cl$_2$, 12 hours; (iii) H$_2$O/Na$_2$CO$_3$; (iv) AgNO$_3$/CH$_3$CN, 12 hours. (v) 3-morpholinopropan-1-ol/Et$_3$N, CH$_2$Cl$_2$, 12 hours, amb.t.; (vi) H$_2$O/Na$_2$CO$_3$.

EXAMPLE 19

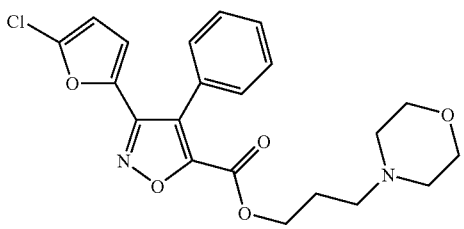

3-(Morpholin-1-yl)propyl[3-(5-chlorofuran-2-yl)-4-phenylisoxazol-5-yl]carboxilate A mixture of thionyl chloride (5 ml) and of [3-(chlorofuran-2-yl)-4-phenylisoxazol-5-yl]carboxylic acid (570 mg, 1.97 mmoles) is kept in reflux conditions for 2 h, then the excess thionyl chloride is removed in a vacuum. To the residue, taken up with methylene chloride (5 ml) and cooled with an ice bath, are added NEt$_3$ (0.26 ml) and 4-(3-hydroxypropyl)morpholine (0.3 ml, 2.17 mmoles). The reaction mixture is kept stirring at ambient temperature for 20 h. The reaction is blocked by adding H$_2$O. The reaction mixture is alkalinised with a saturated solution of Na$_2$CO$_3$ and extracted with methylene chloride. The extracts are combined, dried and concentrated in a vacuum. 702 mg of crude product are obtained which are chromatographed on silica gel (eluent:petroleum ether/ethyl acetate=9:1). 591 mg of product are obtained, 72% yield. M.p. 82.0-83.7° C. FT-IR (KBr): 3140, 3059, 2958, 2854, 2813, 1738, 1690, 1624, 1519, 1447, 1347, 1305, 1239, 1208, 1191, 1118, 1020, 985, 941, 900, 863, 792, 700 cm$^{-1}$. $^1$H NMR (300 MHz, CDCl$_3$, δ): 7.46-7.43 (m, 3H, aromatic protons); 7.33-7.30 (m, 2H, aromatic protons); 6.10 (d, J=3.4 Hz, 1H, furyl proton); 6.08 (d, J=3.4 Hz, 1H, furyl proton); 4.30-4.26 (t, J=6.3 Hz, 2H, CH$_2$O); 3.69-3.63 (m, 4H, CH$_2$OCH$_2$); 2.40-2.31 (m, 4H, CH$_2$NCH$_2$); 2.19-2.15 (t, J=7.1 Hz, 2H, CH$_2$N); 1.76-1.67 (m, 2H, CH$_2$CH$_2$CH$_2$). $^{13}$C NMR (75 MHz, CDCl$_3$, δ): 156.9, 156.2, 153.8, 142.3, 139.5, 130.0, 129.4, 128.8, 128.0, 122.8, 115.0, 108.4, 67.1, 64.6, 55.1, 53.7, 25.5. GC-MS (70 eV) m/z (rel.int.): 418 [M($^{37}$Cl)$^+$, 2], 416 [M($^{35}$Cl)$^+$, 4], 100 (100). Anal. Calc. for C$_{15}$H$_{10}$ClNO$_4$: C, 60.51; H, 5.08; N, 6.72. Found: C, 60.55; H, 5.10; N, 6.69.

FT-IR (KBr) hydrochloride: 3150, 2956, 2863, 2595-2400, 1746, 1630, 1606, 1521, 1446, 1412, 1388, 1346, 1307, 1253, 1206, 1182, 1133, 1101, 1019, 981, 938, 897, 868, 798, 707 cm$^{-1}$.

EXAMPLE 20

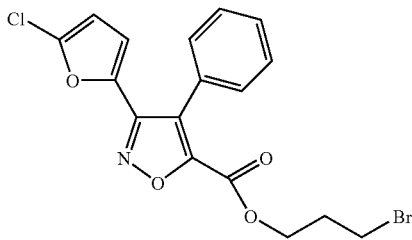

3-Bromopropyl[3-(5-chlorofuran-2-yl)-4-phenylisoxazol-5-yl]carboxylate

A mixture of thionyl chloride (2 ml) and of [3-(chlorofuran-2-yl)-4-phenylisoxazol-5-yl]carboxylic acid (239 mg, 0.83 mmoles) is kept in reflux conditions for 2 hours, then the excess thionyl chloride is removed in a vacuum. To the residue, taken up with methylene chloride (5 ml) and cooled with an ice bath, are added NEt$_3$ (83.83 mg, 0.83 mmoles) and 3-bromo-1-propanol (116 mg, 0.83 mmoles). The reaction mixture is kept stirring at ambient temperature for 12 h. The reaction is blocked by adding H$_2$O. The reaction mixture is alkalinised with a saturated solution of Na$_2$CO$_3$ and extracted with CHCl$_3$. The extracts are combined, dried and concentrated in a vacuum. 235 mg of product are obtained (60% yield). M.p. 100-101° C. FT-IR (KBr): 3136, 3076, 2963, 2924, 1737, 1623, 1605, 1519, 1448, 1463, 1424, 1413, 1385, 1345, 1310, 1249, 1209, 1184, 1152, 1019, 985, 944, 901, 884, 793, 773, 702 cm$^{-1}$. $^1$H NMR (400 MHz, CDCl$_3$, δ): 7.49-7.45 (m, 3H, aromatic protons); 7.33-7.30 (m, 2H, aromatic protons); 6.11 (d, J=3.6 Hz, 1H, furyl proton); 6.07 (d, J=3.6 Hz, 1H, furyl proton); 4.34-4.32 (t, J=6.1 Hz, 2H, COOCH$_2$); 3.07-3.04 (t, J=6.1 Hz, 2H, CH$_2$Br); 2.06-2.00 (quintet, J=6.1 Hz, 2H, CH$_2$CH$_2$CH$_2$). $^{13}$C NMR (100 MHz, CDCl$_3$, δ): 156.7, 156.0, 153.8, 142.2, 139.6, 129.9, 129.5, 128.9, 128.0, 123.0, 115.1, 108.4, 63.8, 31.3, 29.0. GC-MS (70 eV) m/z (rel.int.): 411 [(M$^+$+2), 18], 409 (M$^+$, 18), 282 (10), 281 (12), 244 (10), 207 (11), 188 (12), 153 (13), 152 (22), 145 (100), 118 (32), 89 (36), 73 (16), 63 (11), 44 (12), 41 (12). Anal. Calc. for C$_{17}$H$_{13}$BrClNO$_4$: C, 49.72; H, 3.17; N, 3.41. Found: C, 49.70; H, 3.15; N, 3.39.

EXAMPLE 21

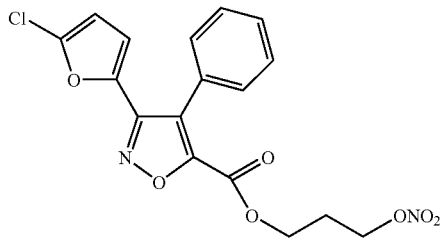

3-(Nitroxy)propyl[3-(5-chlorofuran-2-yl)-4-phenylisoxazol-5-yl]carboxylate

To the solution of 3-bromopropyl [3-(5-chlorofuran-2-yl)-4-phenylisoxazol-5-yl]carboxylate (200 mg, 0.49 mmoles) in CH$_3$CN (1 ml) AgNO$_3$ is added in small amounts (92 mg). The reaction mixture is kept stirring at ambient temperature for 12 hours and then more AgNO$_3$ is added in small amounts (92 mg). The reaction is blocked after 10 hours by filtering AgBr. After having distilled in a vacuum the reaction CH$_3$CN and that used to wash the AgBr, 180 mg of crude product are obtained which are chromatographed on silica gel (eluent: petroleum ether/ethyl acetate=9:1). 145 mg of product are obtained (76% yield). M.p. 79.0-79.8° C. FT-IR (liquid film): 3144, 3055, 2925, 2853, 1740, 1631, 1518, 1447, 1414, 1346, 1306, 1280, 1209, 1188, 1156, 1021, 863, 700 cm$^{-1}$. $^1$H NMR (300 MHz, CDCl$_3$, δ): 7.52-7-45 (m, 3H, aromatic protons); 7.37-7-30 (m, 2H, aromatic protons); 6.13 (d, J=3.4 Hz, 1H, furyl proton); 6.10 (d, J=3.4 Hz, 1H, furyl proton); 4.34-4.30 (t, J=6.2 Hz, 2H, COOCH$_2$); 4.18-4.14 (t, J=6.2 Hz, 2H, CH$_2$ONO$_2$); 2.00-1.92 (quintet, J=6.2 Hz, 2H, CH$_2$CH$_2$CH$_2$). $^{13}$C NMR (75 MHz, CDCl$_3$, δ): 156.5, 155.8, 153.9, 142.2, 139.6, 129.9, 129.6, 128.9, 128.0, 123.2, 115.2, 108.4, 69.2, 61.8, 26.2. GC-MS (70 eV) m/z (rel.int.): 331 [(M($^{37}$Cl)$^+$–63, 37], 329 [M($^{35}$Cl)$^+$–63, 100], 315 (31), 244 (37), 216 (17), 207 (11), 188 (27), 153 (23), 145 (16), 128 (11), 127 (12), 89 (37), 86 (20), 63 (10), 51 (11), 43 (36), 41 (14). Anal. Calc. for C$_{17}$H$_{13}$ClN$_2$O$_7$: C, 51.99; H, 3.34; N, 7.13. Found: C, 52.00; H, 3.35; N, 7.19.

Scheme 7

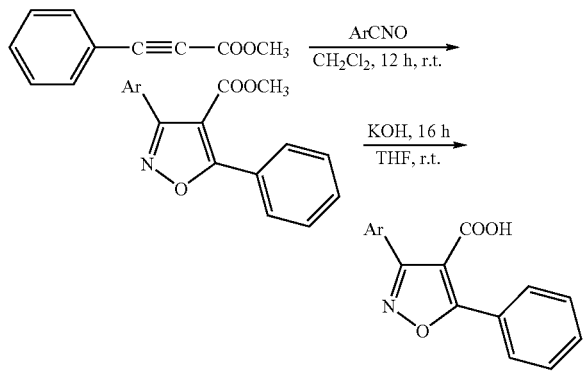

EXAMPLE 22

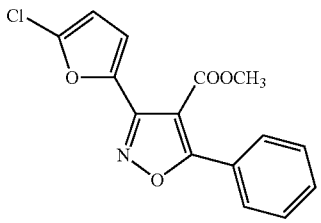

Methyl3[-(5-chlorofuran-2-yl)-5-phenylisoxazol-4-yl]carboxylate

The 2-(5-chlorofuryl)carbonitrile oxide (0.99 mmoles) just prepared is added to the methyl 3-phenylpropiolate (159 mg, 0.99 mmoles) in anhydrous methylene chloride (5 ml) kept stirring at ambient temperature in an atmosphere of $N_2$. The reaction mixture is kept stirring for 72 h, then blocked by adding $H_2O$ and the phases are separated. The aqueous phase is extracted with methylene chloride. The organic phases are combined, dried with anhydrous $Na_2SO_4$ and then the solvent is distilled in a vacuum. Chromatography is performed on silica gel (eluent:petroleum ether/ethyl acetate=10:1). 162 mg of product are obtained (54% yield). M.p. 113-117° C. (dec. 86.4° C.). FT-IR (KBr): 3113, 3050, 2924, 2853, 1723, 1610, 1515, 1491, 1444, 1430, 1346, 1314, 1235, 1210, 1128, 1050, 1019, 937, 805, 776, 687 cm$^{-1}$. $^1$H NMR (300 MHz, CDCl$_3$, δ): 7.84-7.80 (m, 2H, aromatic protons); 7.57-7.47 (m, 3H, aromatic protons); 7.22 (d, J=3.6 Hz, 1H, furyl proton); 6.34 (d, J=3.6 Hz, 1H, furyl proton); 3.84 (s, 3H, CH$_3$). $^{13}$C NMR (75 MHz, CDCl$_3$, δ): 173.0, 162.4, 153.3, 142.2, 139.3, 131.7, 128.9, 128.8, 126.7, 116.3, 108.6, 106.9, 52.5. GC-MS (70 eV) m/z (rel.int.): 305 [(M($^{37}$Cl)$^+$, 14], 303 [M($^{35}$Cl)$^+$, 39], 240 (5), 105 (100), 77 (38), 51 (7). Anal. Calc. for C$_{15}$H$_{10}$ClNO$_4$: C, 59.32; H, 3.32; N, 4.61. Found: C, 59.31; H, 3.30; N, 4.60.

EXAMPLE 23

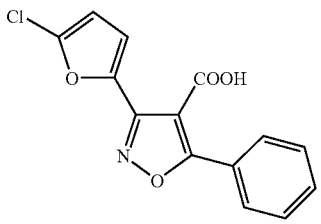

[3-(5-chlorofuran-2-yl)-5-phenylisoxazol-4-yl]carboxylic acid

A solution of KOH (30 mg, 0.475 mmoles) in water (2.5 ml) is added to the [3-(chlorofuran-2-yl)-5-phenylisoxazol-4-yl]methyl carboxylate The reaction mixture is kept stirring overnight at ambient temperature. The reaction is blocked by distilling the THF at a reduced pressure. Ethyl ether is added to the residue. The two phases are separated. The aqueous phase, acidified with 10% HCl, is extracted three times with ethyl ether. The combined organic phases are dried over anhydrous $Na_2SO_4$ and the solvent evaporated at a reduced pressure to give 55 mg of crude product, which is crystallised from chloroform/hexane. 40 mg of needle-shaped white product are obtained (59% yield). $^1$H NMR (300 MHz, CDCl$_3$, δ): 7.87-7.84 (m, 2H, aromatic protons); 7.60-7.49 (m, 3H, aromatic protons); 7.30 (d, J=3.6 Hz, 1H, furyl proton); 7.20-7.00 (bs, 1 H, COOH: exchange with D$_2$O); 6.34 (d, J=3.6 Hz, 1H, furyl proton). $^{13}$C NMR (75 MHz, CDCl$_3$, δ): 174.5, 166.2, 153.5, 141.8, 139.6, 132.0, 129.5, 128.8, 126.4, 117.3, 108.6, 106.0. Anal. Calc. for C$_{14}$H$_8$ClNO$_4$: C, 58.05; H, 2.78; N, 4.83. Found: C, 58.01; H, 2.81; N, 4.85.

EXAMPLE 24

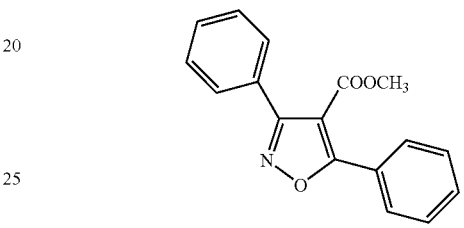

[3,5-diphenylisoxazole-4-yl]methyl carboxylate

The benzonitrile oxide (0.98 mmoles) just prepared is added to the methyl 3-phenylpropiolate (157 mg, 0.98 mmoles) in anhydrous methylene chloride (5 ml) kept stirring at ambient temperature in an atmosphere of $N_2$. The reaction mixture is kept stirring for 12 h, then blocked by adding $H_2O$, The phases are separated and the aqueous phase is extracted with methylene chloride. The organic phases are combined, dried with anhydrous $Na_2SO_4$ and the solvent is distilled in a vacuum. Chromatography is performed on silica gel (eluent: petroleum ether/ethyl acetate=10:1). 184 mg of product are obtained (67% yield). M.p. 102.5-104.8° C. FT-IR (KBr): 3062, 2958, 1729, 1610, 1593, 1573, 1494, 1448, 1408, 1320, 1237, 1188, 1120, 1076, 1043, 941, 806, 768, 726, 697 cm$^{-1}$. $^1$H NMR (300 MHz, CDCl$_3$, δ): 7.96-7.88 (m, 2H, aromatic protons); 7.70-7.63 (m, 2H, aromatic protons); 7.56-7.46 (m, 6H, aromatic protons); 3.72 (s, 3H, CH$_3$). $^{13}$C NMR (75 MHz, CDCl$_3$, δ): 172.7, 163.2, 163.1, 131.6, 130.2, 129.1, 128.9, 128.8, 128.7, 128.6, 127.1, 102, 52.2. GC-MS (70 eV) m/z (rel.int.): 279 (M$^+$, 79), 278 (17), 251 (6), 220 (5), 202 (7), 143 (10), 105 (100), 77 (47), 51 (9). Anal. Calc. for C$_{17}$H$_{13}$NO$_3$: C, 73.11; H, 4.69; N, 5.02. Found: C, 73.06; H, 4.67; N, 5.06.

EXAMPLE 25

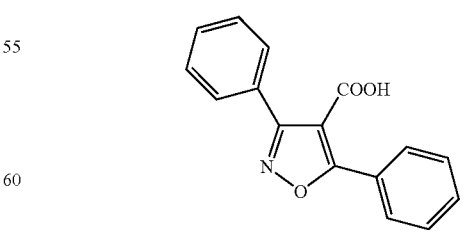

[3,5-diphenylisoxazole-4-yl]carboxylic acid

A solution of KOH (72 mg, 1.28 mmoles) in water (5 ml) is added to the [3.5-diphenylisoxazol-4-yl]methyl carboxylate (180 mg, 0.64 mmoles) in THF (5 ml). The reaction mixture is kept stirring overnight at ambient temperature. The reaction is blocked by distilling the THF at a reduced pressure. Ethyl ether is added to the residue. The two phases are separated. The aqueous phase, acidified with 10% HCl, is extracted three times with ethyl ether. The combined organic phases are dried over anhydrous $Na_2SO_4$ and the solvent evaporated at a reduced pressure to give 148 mg of pulverulent white product with a yield of 87%. FT-IR (KBr): 3600-2800, 1738, 1586, 1567, 1492, 1448, 1417, 1283, 1229, 1119, 756, 730, 692 $cm^{-1}$. $^1H$ NMR (500 MHz, acetone-$d_6$, δ): 8.00-7.98 (m, 2H, aromatic protons); 7.75-7.73 (m, 2H, aromatic protons); 7.66-7.32 (m, 7H, six aromatic protons and the COOH proton which exchanges with $D_2O$). $^{13}C$ NMR (75 MHz, acetone-$d_6$, δ): 172.0, 163.1, 162.8, 131.5, 130.0, 129.1, 129.1, 128.9, 128.8, 128.5, 127.3, 108.8. GC-MS (70 eV) m/z (rel.int.): 221 ($M^+$–44, 55), 146 (13), 144 (25), 142 (15), 133 (10), 132 (33), 105 (100), 103 (11), 91 (17), 89 (22), 77 (39), 50 (19), 44 (28), 41 (19). Anal. Calc. for $C_{16}H_{11}NO_3$: C, 72.44; H, 4.18; N, 5.28. Found: C, 72.46; H, 4.17; N, 5.30.

According to the invention, the following compounds were also synthesised, prepared according to the examples listed below, also as a non-limiting example.

EXAMPLE 26

3-(5-Chlorofuran-2-yl)-4-phenyl-5-methylisoxazole (P6)

Synthesis was carried out using in sequence the two general procedures already described. Yellow crystals are obtained with a 60% yield. M.p. 71-73° C. FT-IR (KBr): 3147, 3051, 2927, 2848, 1633, 1520, 1435, 1412, 1236, 1204, 1134, 1020, 985, 940, 926, 897, 796, 775, 704 $cm^{-1}$. $^1H$ NMR ($CDCl_3$, δ): 2.36 (s, 3H); 6.11-6.12 (d, 1H, J=3.57 Hz); 6.25-6.27 (d, 1H, J=3.57 Hz); 7.25-7.30 (m, 2H, aromatic protons); 7.40-7.47 (m, 3H, aromatic protons). $^{13}C$ NMR (75 MHz, $CDCl_3$, δ): 11.4, 108.1, 113.9, 115.0, 128.6, 129.0, 129.6, 130.2, 138.6, 143.8, 152.4, 167.1. GC-MS (70 eV) m/z (rel.int.): 261 [$M(^{37}Cl)^+$, 5], 259 [$M(^{35}Cl)^+$, 15], 219 (11), 217 (36), 154 (17), 127 (10), 115 (5), 102 (5), 89 (14), 77 (9), 63 (10), 51 (12), 43 (100).

EXAMPLE 27

3,4-Diphenyl-5-methylisoxazole (P10)

Synthesis was carried out using in sequence the two general procedures already described. Yellow crystals are obtained with an 80% yield. M.p. 97-98° C. (hexane), white crystals. FT-IR (KBr): 3051, 2928, 1619, 1597, 1573, 1497, 1464, 1436, 1414, 1376, 1304, 1239, 1074, 915, 769, 696 $cm^{-1}$. $^1H$ NMR ($CDCl_3$, δ): 2.45 (s, 3H); 7.17-7.47 (m, 10H). $^{13}C$ NMR (75 MHz, $CDCl_3$, δ): 11.8, 116.0, 127.9, 128.7, 128.9, 129.4, 129.6, 130.0, 130.6, 161.4, 166.8. GC-MS (70 eV) m/z (rel.int.): 235 ($M^+$, 100), 220 (28), 194 (14), 193 (90), 192 (37), 165 (28), 103 (10), 90 (12), 89 (62), 78 (10), 77 (24), 63 (23), 51 (48), 43 (70).

EXAMPLE 28

Synthesis of 3,4-diphenyl-5-ethylisoxazole (P9)

n-Butyllithium in hexane (2.19M, 0.213 mL, 0.4675 mmol) is added to 3,4-diphenyl-5-methylisoxazole (P10, 0.100 g, 0.425 mmol) in THF (5 mL) kept stirring at –78° C. in a nitrogen atmosphere. The reaction mixture obtained is kept stirring for 1 hour at –78° C. before adding $CH_3I$ (4.25 mmol). The reaction mixture is brought to ambient temperature and then blocked by adding an aqueous solution of $NH_4Cl$. The two phases are separated and the aqueous phase is extracted three times with ethyl acetate. The combined organic extracts are dried over $Na_2SO_4$ and the solvent is then evaporated in a vacuum. The residue is subjected to column chromatography (silica gel, petroleum ether:ethyl acetate=10/1) and 3,4-diphenyl-5-ethylisoxazole is obtained with a yield of 75%. M.p. 85-87° C. (hexane), white crystals. FT-IR (KBr): 3029, 3005, 2923, 2848, 1625, 1596, 1493, 1467, 1437, 1410, 1327, 1282, 1210, 1011, 905, 771, 702 $cm^{-1}$. $^1H$ NMR (200 MHz, $CDCl_3$, δ): 1.29 (t, 3H), 2.78 (q, 2H); 7.12-7.43 (m, 10H). $^{13}C$ NMR (75 MHz, $CDCl_3$, δ): 12.5, 19.7, 115.2, 127.9, 128.7, 128.9, 129.4, 129.5, 130.2, 130.7, 161.3, 171.4. GC-MS (70 eV) m/z (rel.int.): 249 [$M^+$, 100], 234 (6), 221 (18), 220 (99), 194 (9), 193 (61), 192 (46), 165 (17), 115 (7), 103 (8), 89 (53), 77 (15), 63 (10), 51 (10).

General Procedure for Assessing the Activity ($IC_{50}$) COX-1 and COX-2

Fourteen healthy volunteers (25-34 years) were enrolled to take part in the study and were studied on various occasions. Peripheral venous blood samples were taken from donors who had not taken FANS in the 2 weeks prior to the study.

Biosynthesis of $TXB_2$ in the Whole Blood as an Index of Platelet COX-1 Activity 1 ml aliquots of whole blood were immediately transferred into glass test tubes and left to coagulate at 37° C. for 60 minutes. The serum was separated by centrifugation (10 min at 3000 rpm) and kept at –70° C. until the time of dosing the $TXB_2$ with the RIA, as index of maximum stimulation of platelet COX-1 activity, in response to endogenously formed thrombin (Patrono C. et al. Thromb Res. 1980; 17:317-327).

Biosynthesis of $PGE_2$ in the Whole Blood as an Index of Monocyte COX-2 Activity Induced by LPS.

The contribution of platelet COX-1 was suppressed by pretreating the subjects with aspirin 300 mg 48 hours before taking the sample. Aliquots of 1 ml of whole blood taken from the cubital vein with a syringe containing heparin (20 IU/ml blood) were incubated with lipopolysaccharide (LPS, from Escherichia coli 026:B6; Sigma Chemical Company, St. Louis, Mo.) (10 µg/ml) for 24 hours at 37° C. The plasma was separated by centrifugation and kept at –70° C. The $PGE_2$ was measured with a specific radioimmunological assay (RIA) as an index of monocyte COX-2 activity induced by LPS. The production of $PGE_2$, in the whole blood stimulated by LPS, was corrected with the levels of $PGE_2$ measured in the absence of LPS (Patrignani P. et al., J. Pharmacol. Exp. Ther. 1994; 271:1705-12).

Effect of the Compounds on COX-2 and COX-1 Activities in Human Whole Blood in vitro The compounds were dissolved in DMSO and aliquots of 2 microliters were pipetted directly into the test tubes to have final concentrations of 0.001-1000 microM. From 3 to 7 concentrations of each compound were incubated with heparinised whole blood in the presence of LPS (10 microg/ml) for 24 hours at 37° C. or with blood samples left to coagulate for 1 hour at 37° C. to assess the concentration-dependent inhibition of COX-2 vs COX-1, respectively (Patrignani P. et al. J. Pharmacol. Exp. 1994; 271:1705-12; Patrono C, et al. Thromb Res 1980; 17:317-27).

Quantitative Analysis of PGE2 and TXB2

The levels of PGE2 and TXB2 were measured by means of previously described and validated radioimmunological assays (Patrignani P., et al J. Clin. Invest. 1982; 69:1366-72; Ciabattoni G. et al. J. Endocrinol. Invest. 1979; 2:173-182).

TABLE

Activity of diarylisoxazoles obtained with the whole blood method.

(1)

| Compound | $R_1$ | $R_2$ | $R_3$ | COX-1 IC$_{50}$(µM)$^a$ | COX-2 IC$_{50}$(µM)$^a$ |
|---|---|---|---|---|---|
| Example 5 | 5-chloro-2-furyl- | Ph | CF$_3$ | 0.81 (n = 3) | >100 (n = 3) |
| Example 6 | 5-chloro-2-furyl- | 4-F-Ph | CH$_3$ | 1.9 (n = 3) | >100 (n = 3) |
| Example 7 | 5-chloro-2-furyl- | 2-F-Ph | CH$_3$ | 1.9 (n = 3) | >100 (n = 3) |
| Example 17 | 5-chloro-2-furyl- | Ph | CH$_2$OH | 4.2 (n = 2) | a 100 µM, I = 44% (n = 2) |
| Example 18 | 5-chloro-2-furyl- | Ph | CH$_2$OCOCH$_3$ | 5.2 (n = 3) | >100 (n = 2) |
| Example 26 (P6) | 5-chloro-2-furyl- | Ph | CH$_3$ | 0.5 (n = 3) | >100 (n = 3) |
| Example 27 (P10) | Ph- | Ph | CH$_3$ | 0.090 (n = 3) | 2.49 (n = 3) |
| Example 28 (P9) | Ph- | Ph | CH$_3$CH$_2$ | 0.05 (n = 3) | 1.49 (n = 3) |
| Valdecoxib | Ph- | PhSO$_2$NH$_2$ | CH$_3$ | 27 (n = 10) | 0.57 (n = 10) |

$^a$The value of "n" indicates the number of experiments carried out for each compound.

Results

The table shows the value of IC$_{50}$ for COX-1 and COX-2 obtained with the human blood model for some diarylheterocycles with general formula (1).

The invention claimed is:

1. A diarylisoxazole derivative which is selected from
   3-(5-Chlorofuran-2-yl)-4-phenyl-5-(trifluoromethyl)isoxazole;
   3-(5-Chlorofuran-2-yl)-4-(4-fluorophenyl)-5-methylisoxazole;
   3-(5-Chlorofuran-2-yl)-4-(2-fluorophenyl)-5-methylisoxazole;
   3-(2-Chlorophenyl)-4-(2-fluorophenyl)-5-methylisoxazole;
   [3-(5-Chlorofuran-2-yl)-4-phenylisoxazol-5-yl]carboxylic acid;
   Methyl [3-(5-chlorofuran-2-yl)-4-phenylisoxazol-5-yl]carboxylate;
   3-(5-Chlorofuran-2-yl)-4-phenyl-5-hydroxymethylisoxazole;
   5-Acetoxymethyl-3-(5-chlorofuran-2-yl)-4-phenylisoxazole;
   3-(Morpholin-1-yl)propyl [3-(5-chlorofuran-2-yl)-4-phenylisoxazol-5-yl]carboxilate;
   3-Bromopropyl [3-(5-chlorofuran-2-yl)-4-phenylisoxazol-5-yl]carboxylate;
   3-(Nitroxy)propyl [3-(5-chlorofuran-2-yl)-4-phenylisoxazol-5-yl]carboxylate;
   Methyl 3 [-(5-chlorofuran-2-yl)-5-phenylisoxazol-4-yl] carboxylate; and
   [3-(5-Chlorofuran-2-yl)-5-phenylisoxazol-4-yl]carboxylic acid.

2. Pharmaceutical composition comprising at least a compound according to claim 1.

* * * * *